United States Patent
Ohashi et al.

(10) Patent No.: US 11,596,374 B2
(45) Date of Patent: Mar. 7, 2023

(54) X-RAY DIAGNOSTIC APPARATUS AND MEDICAL-INFORMATION PROCESSING APPARATUS

(71) Applicant: CANON MEDICAL SYSTEMS CORPORATION, Otawara (JP)

(72) Inventors: Shumpei Ohashi, Otawara (JP); Junichi Yamagishi, Nasushiobara (JP); Naotaka Sato, Otawara (JP); Jun Sakakibara, Otawara (JP); Yusuke Kanno, Nasushiobara (JP); Toshiya Waku, Yaita (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 33 days.

(21) Appl. No.: 17/232,281

(22) Filed: Apr. 16, 2021

(65) Prior Publication Data

US 2021/0321966 A1 Oct. 21, 2021

(30) Foreign Application Priority Data

Apr. 16, 2020 (JP) .............................. JP2020-073301

(51) Int. Cl.
*A61B 6/00* (2006.01)

(52) U.S. Cl.
CPC .............. *A61B 6/481* (2013.01); *A61B 6/469* (2013.01); *A61B 6/504* (2013.01); *A61B 6/544* (2013.01)

(58) Field of Classification Search
None
See application file for complete search history.

(56) References Cited

U.S. PATENT DOCUMENTS

| | | | |
|---|---|---|---|
| 2012/0229504 A1 | 9/2012 | Nakamura et al. | |
| 2015/0250437 A1 | 9/2015 | Zaiki | |
| 2017/0319150 A1 | 11/2017 | Goto et al. | |
| 2018/0070902 A1* | 3/2018 | Lin | A61B 5/1079 |
| 2019/0012932 A1 | 1/2019 | Higaki et al. | |
| 2020/0037972 A1* | 2/2020 | Imagawa | A61B 6/487 |
| 2020/0170609 A1* | 6/2020 | Hikosaka | G06F 11/0727 |
| 2021/0145391 A1* | 5/2021 | Hoornaert | G16H 50/20 |

FOREIGN PATENT DOCUMENTS

| | | |
|---|---|---|
| JP | 2011-161091 A | 8/2011 |
| JP | 2012-147934 A | 8/2012 |
| JP | 2013-013649 A | 1/2013 |
| JP | 2014-128633 A | 7/2014 |
| JP | 2017-074194 A | 4/2017 |
| JP | 2017-202311 A | 11/2017 |
| JP | 2019-013296 A | 1/2019 |
| JP | 2019-055004 A | 4/2019 |

* cited by examiner

*Primary Examiner* — Hoon K Song
(74) *Attorney, Agent, or Firm* — Oblon, McClelland, Maier & Neustadt, L.L.P.

(57) ABSTRACT

An X-ray diagnostic apparatus of an embodiment includes processing circuitry. The processing circuitry determines a concentration of a contrast agent in contrast-enhanced image collection based on first reference information in which a recommended contrast in a contrast-enhanced image is associated with each region of interest to be subject to collection of the contrast-enhanced image, and on second reference information that indicates a relation among a generation condition of an X-ray, a concentration of a contrast agent, and a contrast. The processing circuitry calculates setting information of an injector to inject a contrast agent to the subject based on the determined concentration of a contrast agent.

15 Claims, 12 Drawing Sheets

FIG.2A

| REGION OF INTEREST | REPRESENTATIVE BLOOD VESSEL DIAMETER | OPTIMAL CONTRAST |
|---|---|---|
| HEAD | 1.0 mm | 2 |
| ABDOMEN (LIVER) | 3.0 mm | 1.5 |
| | | |

FIG.2B

| BODY THICKNESS (CONVERTED INTO WATER) | BLOOD VESSEL DIAMETER | X-RAY TUBE VOLTAGE | CONTRAST | CONCENTRATION OF CONTRAST AGENT |
|---|---|---|---|---|
| 10 cm | 1.0 mm | 80 kV | 0.5 | 20 mg/ml |
| 10 cm | 1.0 mm | 80 kV | 1 | 30 mg/ml |
| | | | | |

FIG.3

PART OF INTEREST:
BLOOD VESSEL DIAMETER:
BODY THICKNESS:
CONTRAST:
CONCENTRATION OF CONTRAST AGENT (mg/ml):
DILUTION RATIO:

RECOMMENDED
CONCENTRATION OF
CONTRAST AGENT: 0.4 ml/s

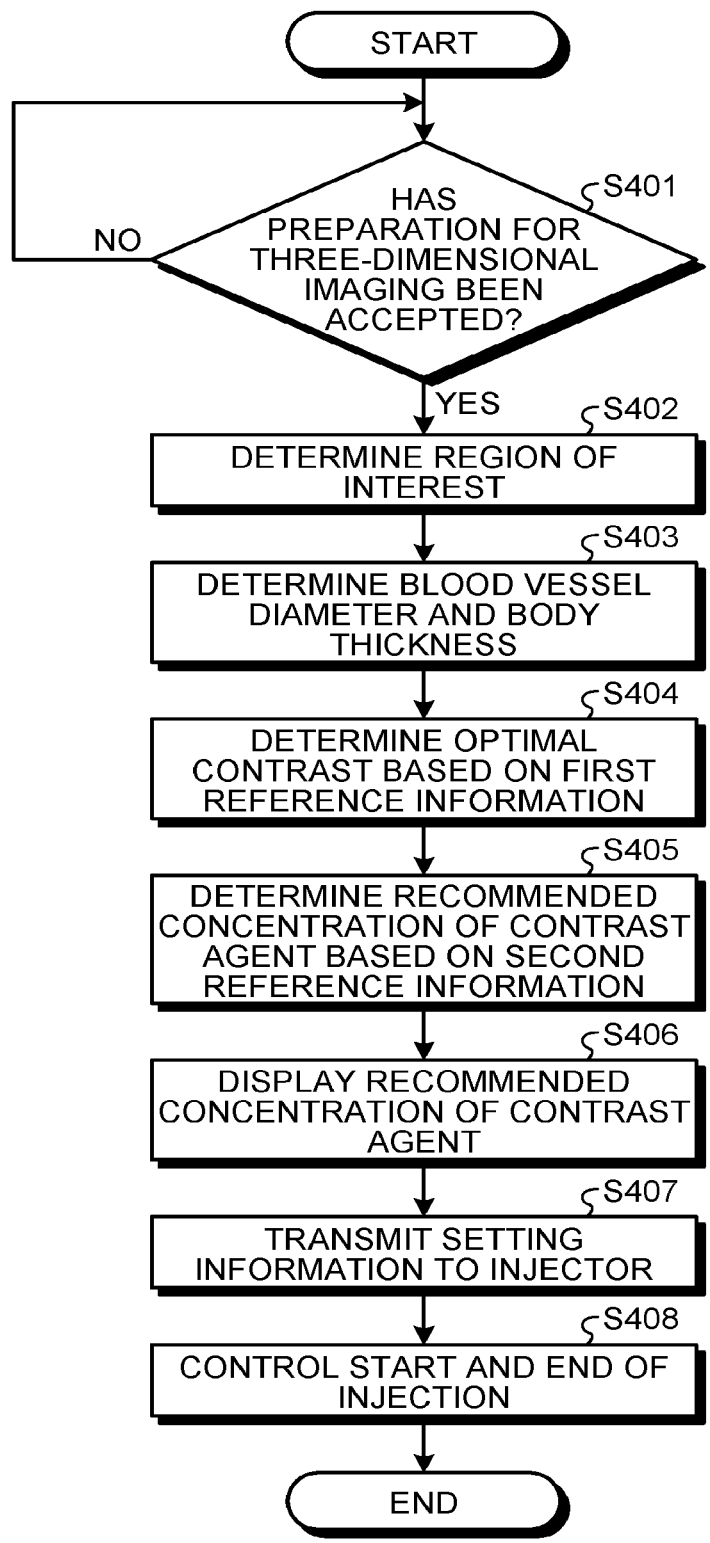

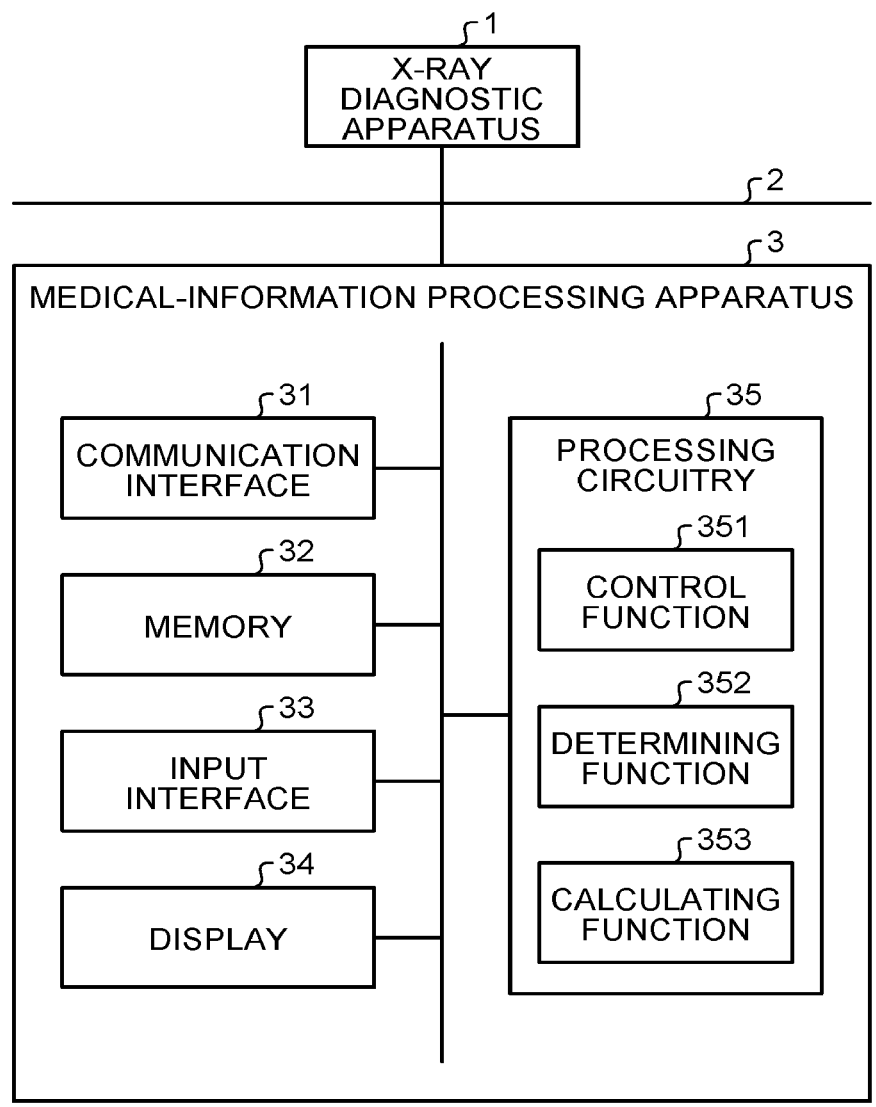

X-RAY DIAGNOSTIC APPARATUS AND MEDICAL-INFORMATION PROCESSING APPARATUS

CROSS-REFERENCE TO RELATED APPLICATIONS

This application is based upon and claims the benefit of priority from Japanese Patent Application No. 2020-073301, filed on Apr. 16, 2020; the entire contents of which are incorporated herein by reference.

FIELD

Embodiments disclosed in the present specification and the drawings relate to an X-ray diagnostic apparatus and a medical-information processing apparatus.

BACKGROUND

In X-ray diagnostic apparatuses, contrast-enhanced imaging has conventionally been performed in which a catheter is inserted in a blood vessel of a subject, and a contrast agent is injected from an injector, to collect an X-ray image. In the contrast-enhanced imaging, for example, injection conditions, such as a dilution ratio and an injection speed of a contrast agent, are determined for each part to be imaged based on experience, and are set to the injector.

BRIEF DESCRIPTION OF THE DRAWINGS

FIG. 2A is a diagram illustrating an example of first reference information according to the first embodiment;

FIG. 2B is a diagram illustrating an example of second reference information according to the first embodiment;

FIG. 3 is a diagram illustrating an example of display information according to the first embodiment;

FIG. 11 is a flowchart illustrating a procedure of processing performed by the X-ray diagnostic apparatus according to the fifth embodiment; and FIG. 12 is a diagram illustrating an example of a configuration of a medical-information processing apparatus according to another embodiment.

DETAILED DESCRIPTION

According to an embodiment, an X-ray diagnostic apparatus includes processing circuitry. The processing circuitry is configured to determine a concentration of a contrast agent in contrast-enhanced image collection based on first reference information in which a recommended contrast in a contrast-enhanced image is associated with each region of interest to be subject to collection of the contrast-enhanced image, and on second reference information that indicates a relation among a generation condition of an X-ray, a concentration of a contrast agent, and a contrast. The processing circuitry is configured to calculate setting information of an injector to inject a contrast agent to the subject based on the determined concentration of a contrast agent.

Hereinafter, embodiments of an X-ray diagnostic apparatus and a medical-information processing apparatus will be explained in detail with reference to the drawings. The X-ray diagnostic apparatus and the medical-information processing apparatus according to the present application are not limited to the embodiments described below. Moreover, the embodiments can be combined with other embodiments or conventional techniques within a range not causing a contradiction in processing. Furthermore, common reference symbols are assigned to like components in the following explanation, and duplicated explanation is omitted.

First Embodiment

Figure 1:
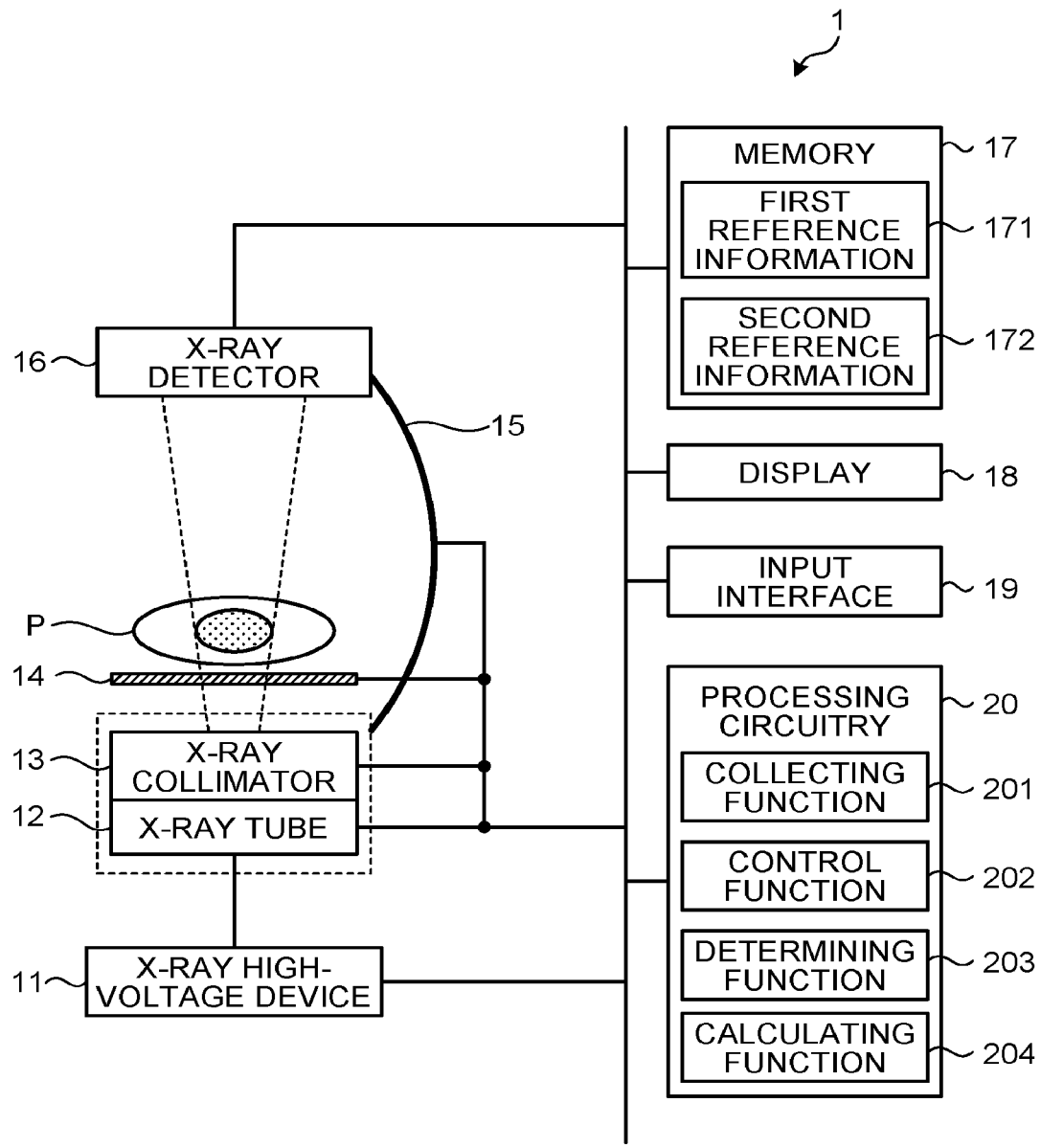
FIG. 1 is a block diagram illustrating an example of a configuration of an X-ray diagnostic apparatus according to a first embodiment.

A configuration of an X-ray diagnostic apparatus according to a first embodiment will be explained. FIG. 1 is a block diagram illustrating an example of a configuration of an X-ray diagnostic apparatus 1 according to a first embodiment. As illustrated in FIG. 1, the X-ray diagnostic apparatus 1 includes an X-ray high-voltage device 11, an X-ray tube 12, an X-ray collimator 13, a table 14, a C-arm 15, an X-ray detector 16, a memory 17, a display 18, an input interface 19, and processing circuitry 20.

The X-ray high-voltage device 11 supplies a high voltage to the X-ray tube 12 under control of the processing circuitry 20. For example, the X-ray high-voltage device 11 includes an electric circuit, such as a transformer and a rectifier, a high-voltage generator that generates a high voltage to be applied to the X-ray tube 12, and an X-ray control device that controls an output voltage according to an X-ray emitted by the X-ray tube 12. The high-voltage generator may be of a transformer type or of an inverter type.

The X-ray tube 12 is a vacuum tube having a cathode (filament) that generates a thermion, and an anode (target) that receives collision of thermions to generate an X-ray. The X-ray tube 12 generates an X-ray by irradiating thermions from the cathode to the anode by using a high voltage supplied from the X-ray high-voltage device 11.

The X-ray collimator 13 includes an X-ray beam aperture that limits an irradiation range of an X-ray generated by the X-ray tube 12, and a filter to adjust an X-ray emitted from the X-ray tube 12.

The X-ray aperture in the X-ray collimator 13 includes, for example, four pieces of slidable aperture blades. The X-ray aperture slides the aperture blades, and thereby limits an X-ray generated by the X-ray tube 12 to be irradiated to a subject P. The aperture blade is a plate-shaped member made from lead or the like, and is arranged near an X-ray irradiation window of the X-ray tube 12 to adjust an irradiation range of an X-ray.

The filter in the X-ray collimator 13 is provided to reduce an exposure dose of the subject P and to improve the image quality of X-ray image data, and changes a quality of X-ray passing therethrough by its material and thickness to reduce low energy components easy to be absorbed by the subject P, or to reduce high energy components that causes reduction in contrast of X-ray image data. Moreover, the filter changes a dose and an irradiation range of an X-ray by its material, thickness, position, and the like, to attenuate X-rays so that an X-ray irradiated to the subject P from the X-ray tube 12 to have a predetermined distribution.

For example, the X-ray collimator 13 includes a driving mechanism of a motor, an actuator, and the like, and controls irradiation of an X-ray by actuating the driving mechanism under control of the processing circuitry 20 described later. For example, the X-ray collimator 13 controls an irradiation range of an X-ray to be irradiated to the subject P by adjusting an aperture of the aperture blades of the X-ray aperture, by applying a driving voltage to the driving mechanism according to a control signal received from the processing circuitry 20. Moreover, for example, the X-ray collimator 13 controls a distribution of a dose of an X-ray to be irradiated to the subject P by adjusting a position of the filter by applying a driving voltage to the driving mechanism according to a control signal received from the processing circuitry 20.

The table 14 is a bed on which the subject P is laid, and is arranged on a bed unit not illustrated. The subject P is not included in the X-ray diagnostic apparatus 1. For example, the bed unit includes a driving mechanism, such as a motor and an actuator, and controls movement and tilting of the table 14 by actuating the driving mechanism under control of the processing circuitry 20. For example, the bed unit moves or tilts the table 14 by applying a driving voltage to the driving mechanism according to a control signal received from the processing circuitry 20.

The C-arm 15 holds the X-ray tube 12 and the X-ray collimator 13, and the X-ray detector 16, so as to oppose to each other sandwiching the subject P. For example, the C-arm 15 includes a driving mechanism, such as a motor and an actuator, and rotates and moves by actuating the driving mechanism under control of the processing circuitry 20. For example, the C-arm 15 rotates and moves the X-ray tube 12, the X-ray collimator 13, and the X-ray detector 16 with respect to the subject P by applying a driving voltage to the driving mechanism according to a control signal received from the processing circuitry 20, to control an irradiation position and an irradiation angle of an X-ray. In FIGS. 2A and 2B, a case in which the X-ray diagnostic apparatus 1 is a single plane type is explained as an example, but embodiments are not limited thereto, and it may be a biplane type.

The X-ray detector 16 is an X-ray flat panel detector (FPD) having detecting devices that are arranged, for example, in a matrix. The X-ray detector 16 detects an X-ray that has been irradiated from the X-ray tube 12, and has passed through the subject P, and outputs a detection signal corresponding to a detected X-ray amount to the processing circuitry 20. The X-ray detector 16 may be an indirect conversion detector including a grid, scintillator array, and an optical sensor array, or may be a direct conversion detector including a semiconductor device that converts an incident X-ray into an electrical signal.

The memory 17 is implemented by, for example, a semiconductor memory device, such as a random access memory (RAM). The memory 17 temporarily stores a processing result by the processing circuitry 20. For example, the memory 17 accepts and temporarily stores various kinds of data, such as X-ray image data, collected by the processing circuitry 20. The X-ray image data in the present application includes the detection signal detected by the X-ray detector 16, projection data that is generated based on the detection signal, and an X-ray image generated based on the projection data.

Furthermore, the memory 17 stores various kinds of information used by the processing circuitry 20. For example, the memory 17 stores first reference information 171 and a second reference information 172 as illustrated in FIG. 1. The first reference information 171 and the second reference information 172 will be described in detail later.

Moreover, the memory 17 stores programs that correspond to respective functions read and executed by the processing circuitry 20. The memory 17 may be implemented by a server group (cloud) that is connected to the X-ray diagnostic apparatus 1 through a network.

The display 18 displays various kinds of information. For example, the display 18 displays a graphical user interface (GUI) to accept an instruction by an operator, or various kinds of X-ray images, under control of the processing circuitry 20. Moreover, the display 18 displays a processing result by the processing circuitry 20. For example, the display 18 displays setting information of an injector. The setting information of the injector will be described in detail later.

The input interface 19 accepts various kinds of input operations from an operator, and converts the accepted input operation into an electrical signal to output to the processing circuitry 20. For example, the input interface 19 is implemented by a mouse, a keyboard, a trackball, a switch, a button, a joystick, a touchpad with which an input operation is performed by touching an operating surface, a touch screen in which a display screen and a touchpad are integrated, a non-contact input circuit using an optical sensor, a voice input circuit, and the like. The input interface 19 may be constituted of a tablet terminal that is capable of wireless communication with an apparatus main unit, or the like. Furthermore, the input interface 19 is not limited to those having a physical operating part, such as a mouse and a keyboard. For example, a processing circuit of an electrical signal that receives an electrical signal corresponding to an input operation from an external input device separately provided from the apparatus, and outputs this electrical signal to the processing circuitry 20 is also included in examples of the input interface 19.

The processing circuitry 20 controls an overall operation of the X-ray diagnostic apparatus 1 by performing a collecting function 201, a control function 202, a determining function 203, and a calculating function 204. Specifically, the processing circuitry 20 executes programs corresponding to the respective functions from the memory 17, to control the operation of the X-ray diagnostic apparatus 1. The processing circuitry 20 is one example of a processing circuit.

The collecting function 201 collects X-ray image data. For example, the collecting function 201 controls the X-ray high-voltage device 11 to adjust a voltage to be supplied to the X-ray tube 12, and thereby controls an X-ray dose to be irradiated to the subject P or ON/OFF. Moreover, the collecting function 201 controls an operation of the X-ray collimator 13 to adjust an aperture of the aperture blades of the X-ray aperture, and thereby controls an irradiation range of an X-ray to be irradiated to the subject P. Specifically, the collecting function 201 can change a shape, a size, and a position of an opening formed by the aperture blades by sliding the aperture blades in the X-ray aperture. For example, the collecting function 201 moves to slide the aperture blades such that an X-ray is irradiated only at a region of interest (ROI) set by a user through the input interface 19.

Furthermore, the collecting function 201 controls the operation of the X-ray collimator 13 to adjust a position of the filter, and thereby controls a distribution of a dose of an X-ray. For example, the collecting function 201 controls the distribution of a dose of an X-ray by moving the filter to a position set by the user through the input interface 19. Moreover, the collecting function 201 controls the operation of the C-arm 15, to rotate or move the C-arm 15. Furthermore, for example, the collecting function 201 controls the operation of the bed unit, and thereby moves or tilts the table 14.

Furthermore, the collecting function 201 generates projection data based on a detection signal received from the X-ray detector 16, and stores the generated projection data in the memory 17. Moreover, the collecting function 201 generates an X-ray image by performing various kinds of image processing with respect to the projection data stored in the memory 17. Furthermore, the collecting function 201 performs, for example, noise reduction processing by an image processing filter, or scattered radiation correction with respect to the X-ray image.

The collecting function 201 can reconstruct three-dimensional image data (volume data) by using the projection data collected by rotational imaging, and can generate an X-ray image from the reconstructed volume data. For example, the collecting function 201 performs rotational imaging to collect projection data at a predetermined frame rate while rotating the C-arm 15, and reconstructs volume data showing a blood vessel shape of the subject P from the collected projection data.

As one example, the collecting function 201 performs rotational imaging with respect to the subject P in a state in which a contrast agent is not injected in blood vessels, and collects mask images at a predetermined frame rate. Furthermore, the collecting function 201 performs rotational imaging with respect to the subject P in a state in which a contrast agent is injected in the blood vessels, and collects contrast images at the predetermined frame rate.

Subsequently, the collecting function 201 reconstructs volume data that shows a blood vessel shape of the subject P by using difference image data by performing subtraction between the mask image and the contrast image. As another example, the collecting function 201 reconstructs volume data by using a mask image. Moreover, the collecting function 201 reconstructs volume data by using a contrast image. Subsequently, the collecting function 201 generates volume data showing a blood vessel shape of the subject P by performing subtraction between the reconstructed two kinds of volume data.

The control function 202 controls the display 18 to display a GUI or an X-ray image. For example, the control function 202 reads an X-ray image from the memory 17 and causes the display 18 to display it in accordance with an operation made through the input interface 19. Moreover, the control function 202 controls transmission and reception of data with an external device through a network not illustrated.

The determining function 203 determines a concentration of a contrast agent according to a region of interest of a subject. Specifically, the determining function 203 determines a concentration of a contrast agent enabling to acquire an optimal contrast in the region of interest. The calculating function 204 calculates setting information of an injector based on the concentration of a contrast agent determined by the determining function 203. The processing of the determining function 203 and the calculating function 204 will be described in detail later.

The overall configuration of the X-ray diagnostic apparatus 1 has so far been explained. With such a configuration, the X-ray diagnostic apparatus 1 enables easy setting of injection conditions of a contrast agent to acquire a desirable contrast by processing of the processing circuitry 20, without depending on experience. Specifically, the X-ray diagnostic apparatus 1 calculates and displays an injection condition of a contrast agent for acquiring an optimal contrast in a region of interest, and thereby enables easy setting of the injection condition of a contrast agent without depending on experience.

As described above, in X-ray diagnostic apparatuses, injection conditions of a contrast agent is determined by experience when contrast-enhanced imaging is performed, and are set to an injector. However, in an actual situation, an acquired contrast varies depending on a body thickness of a subject or a generation condition of an X-ray, and a contrast of a blood vessel can be too low or too high with the set injection conditions. For example, when the contrast is too low, a blood vessel is not clearly rendered, and when the contrast is too high, the brightness of the blood vessel becomes so high that artifacts appear, or peripheral tissues cannot be rendered appropriately if the blood vessel is to be rendered properly. However, performing another imaging again, changing to a different injection condition is not preferable from the viewpoint of a usage amount of a contrast agent, an exposed dose, and a workflow.

Therefore, the X-ray diagnostic apparatus 1 according to the present application calculates and displays an injection condition of a contrast agent that enables to acquire an optical contrast in a region of interest before performing contrast-enhanced imaging. Hereinafter, details of the processing performed by the X-ray diagnostic apparatus 1 will be explained. In the following, a case of performing three-dimensional contrast-enhanced imaging will be explained as an example.

The determining function 203 determines a concentration of a contrast agent in a region of interest of a subject at the time of contrast-enhanced image collection, based on the first reference information in which a recommended contrast in a contrast-enhanced image is associated with each region of interest to be a subject to contrast-enhanced image collection, and the second reference information indicating a relation among a generation condition of an X-ray, a concentration of a contrast agent, and a contrast.

Specifically, the determining function 203 acquires a contrast recommended in a region of interest of a subject from the first reference information, and acquires a concentration of a contrast agent from the second reference information based on the acquired contrast and the generation condition of an X-ray to be irradiated to the subject, to determine the concentration of a contrast agent in the region of interest of the subject at the time of contrast-enhanced image collection.

For example, the determining function 203 first determines a region of interest of a subject to be contrast-enhanced imaged, when determining the concentration of a contrast agent. As an example, the determining function 203 determines a region of interest of the subject based on information about a subject part added to an imaging protocol of the contrast-enhanced imaging, or a size of a field of view in the contrast-enhanced imaging. In three-dimensional contrast-enhanced imaging, for preparation, first, a user operates the input interface 19 to select a field of view (FOV) and an imaging protocol. The determining function 203 determines a region of interest in the subject from the FOV selected by the user, or the information about the imaging protocol.

As a preparation for the three-dimensional contrast-enhanced imaging, for example, preliminary imaging or fluoroscopy for determining an optimal X-ray condition may be performed. In such a case, the determining function 203 can determine a generation condition of an X-ray (for example, an X-ray tube voltage, and the like), or can estimate the body thickness of the subject based on an X-ray image collected by the preliminary imaging or fluoroscopy.

As described above, when a region of interest of the subject is determined, the determining function 203 acquires information about an optical contrast in the determined region of interest based on the first reference information in which a region of interest and an optical contrast are associated with each other. Subsequently, the determining function 203 determines a concentration of a contrast agent in the region of interest of the subject at the time of contrast-enhanced image collection, by referring to the second reference information indicating a relation among a generation condition of an X-ray, a contrast, and a concentration of a contrast agent in a blood vessel. That is, the determining function 203 acquires information of the concentration of a contrast agent in the region of interest from the second reference information by using the acquired information of the optimal contrast, generation condition of an X-ray at the time of contrast-enhanced imaging based on the imaging protocol (or generation condition of an X-ray at the time of contrast-enhanced imaging based on preliminary imaging or fluoroscopy).

The calculating function 204 calculates setting information of an injector that injects a contrast agent to the subject based on the determined concentration of a contrast agent in the region of interest. Specifically, the calculating function 204 calculates an injection condition of a contrast agent based on the generation condition of an X-ray in the contrast-enhanced imaging and the concentration of a contrast agent. For example, the calculating function 204 calculates an injection condition including at least one of an injection speed of a contrast agent to be injected to the subject, and a dilution ratio of the contrast agent.

Determination of the concentration of a contrast agent and calculation of the injection condition of the contrast agent using the first reference information and the second reference information may be done considering a blood vessel diameter or a body thickness. The contrast of a blood vessel in a contrast-enhanced image varies according to the concentration of a contrast agent in the blood vessel, but when a blood vessel diameter varies, if the contrast agent is injected with the same injection condition, the concentration of a contrast agent in the blood vessel becomes lower when the blood vessel diameter is larger, and the contrast is to be low. Moreover, when a body thickness varies, an X-ray tube voltage to collect an appropriate X-ray image varies, and if the X-ray tube voltage is increased, for example, because the body thickness is large, the contrast is to be low. As described, a blood vessel diameter and a body thickness are factors affecting a contrast of a blood vessel in a contrast-enhanced image. Therefore, by determining an injection condition of a contrast agent considering these factors, an injection condition of a higher precision can be calculated.

Hereinafter, one example of calculation of an injection condition when a blood vessel diameter and a body thickness are considered will be explained. FIG. 2A is a diagram illustrating an example of the first reference information 171 according to the first embodiment. The first reference information 171 is an example of first reference information. For example, the first reference information 171 is information in which a representative blood vessel diameter and an optimal contrast are associated with each other for each region of interest as illustrated in FIG. 2A. The region of interest signifies a region including a blood vessel subject to contrast-enhanced imaging. Moreover, the representative blood vessel diameter signifies a blood vessel diameter of a representative blood vessel among blood vessels (blood vessels subject to the contrast-enhanced imaging) included in the region of interest. Moreover, the optimal contrast signifies an optimal contrast between a blood vessel and a peripheral tissue (a pixel value of a contrast-enhanced blood vessel/a pixel value of periphery of the blood vessel) when the blood vessel in the region of interest is contrast-enhanced imaged.

For example, in the first reference information 171, information in which "REGION OF INTEREST: HEAD", "REPRESENTATIVE BLOOD VESSEL DIAMETER: 1.0 mm", AND "OPTIMAL CONTRAST: 2" are associated with one another is stored. This information indicates that the region of interest is "HEAD", the representative blood vessel diameter is "1.0 mm", and the optimal contrast is "2". Similarly, in the first reference information 171, information in which "REGION OF INTEREST: ABDOMEN (LIVER)", "REPRESENTATIVE BLOOD VESSEL DIAMETER: 3.0 mm", AND "OPTIMAL CONTRAST: 1.5" are associated with one another and the like are stored.

Note that the first reference information 171 illustrated in FIG. 2A is only an example, and a format of the information is not limited to the table in FIG. 2A, but may be a database. Moreover, the information of an optimal contrast can be arbitrarily changed by a user. Furthermore, a body thickness may further be stored, associating with the region of interest.

FIG. 2B is a diagram illustrating an example of the second reference information 172 according to the first embodiment. The second reference information 172 is one example of second reference information. For example, the second reference information 172 is information in which a body thickness (converted into water), a blood vessel diameter, an X-ray tube voltage, a contrast, and a concentration of a contrast agent are associated with one another. The body thickness (converted into water) signifies a body thickness of an imaged part. Moreover, the blood vessel diameter signifies a blood vessel diameter of a blood vessel subject to contrast-enhanced imaging. Furthermore, the X-ray tube voltage signifies an X-ray tube voltage of an X-ray to be irradiated to the subject. Furthermore, the contrast signifies a contrast between a contrast-enhanced blood vessel and a peripheral tissue. Moreover, the concentration of a contrast agent signifies a concentration of a contrast agent in a blood vessel.

For example, as illustrated in FIG. 2B, in the second reference information 172, information in which "BODY THICKNESS (CONVERTED INTO WATER): 10 cm", "BLOOD VESSEL DIAMETER; 1.0 mm", "X-RAY TUBE VOLTAGE: 80 Kv", "CONTRAST: 0.5", and "CONCENTRATION OF CONTRAST AGENT: 20 mg/ml" are associated with one another is stored. This information indicates that the concentration of a contrast agent in a blood vessel with which the contrast becomes "0.5" when contrast-enhanced imaging is performed with the X-ray tube voltage of "80 kV" with respect to a region of interest in which the body thickness converted into water is "10 cm" and the blood vessel diameter is "1.0 mm" is "20 mg/ml". Similarly, in the second reference information 172, information in which "BODY THICKNESS (CONVERTED INTO WATER): 10 cm", "BLOOD VESSEL DIAMETER: 1.0 mm", "X-RAY TUBE VOLTAGE: 80 Kv", "CONTRAST: 1", and "CONCENTRATION OF CONTRAST AGENT: 30 mg/ml" are associated with one another and the like are stored. As described, in the second reference information 172, information of an X-ray tube voltage, a contrast, and a concentration of a contrast agent for each of body thickness and blood vessel diameter are stored.

Note that the second reference information 172 illustrated in FIG. 2B is only an example, and it may be any kind of information as long as it is information in which a body thickness, a blood vessel diameter, an X-ray tube voltage, and a contrast are the input data, and a concentration of a contrast agent is the output data. For example, the second reference information 172 may be a database or a series of functions. As a series of functions, for example, a neural network in which parameters are adjusted by a method of machine learning can be used.

The determining function 203 determines a concentration of a contrast agent in the region of interest to be a subject of contrast-enhanced imaging of the subject by using the first reference information 171 illustrated in FIG. 2A and the second reference information 172. For example, the determining function 203 determines a region of interest based on a size of field of view input by a user in preparation for three-dimensional contrast-enhanced imaging, and information about an imaging protocol.

The determining function 203 acquires information of an optimal contrast corresponding to a representative blood vessel diameter in the determined region of interest by referring to the first reference information 171. When information of a representative body thickness in the region of interest is further associated in the first reference information 171, the determining function 203 further acquires the information of a body thickness. Moreover, when a past image of the subject is available, the determining function 203 determines a body thickness in the region of interest of the subject from the past image in the region of interest of the subject, and determines a concentration of a contrast agent in the region of interest of the subject at the time of contrast-enhanced image collection based on the second reference information 172 corresponding to the determined body thickness. For example, when preliminary imaging or fluoroscopy to set a generation condition of an X-ray in contrast-enhanced imaging has been performed, the determining function 203 acquires information of a body thickness in the region of interest of the subject based on an X-ray image collected by the preliminary imaging or fluoroscopy. The determining function 203 determines a concentration of a contrast agent based on the second reference information 172 corresponding to the acquired body thickness.

As described, when information of a body thickness in a region of interest, a blood vessel diameter, and an optimal contrast is acquired, the determining function 203 refers to the second reference information 172 next, and determines a concentration of a contrast agent in a blood vessel that makes a contrast of a contrast-enhanced blood vessel in the region of interest be the optimal contrast. Specifically, the determining function 203 further acquires information of an X-ray tube voltage from the generation condition of an X-ray acquired from the imaging protocol, and acquires information of a concentration of a contrast agent corresponding to the body thickness, the blood vessel diameter, the X-ray tube voltage, and the contrast from the second reference information 172, to thereby determine the concentration of a contrast agent in the blood vessel to make the contrast of the contrast-enhanced blood vessel in the region of interest be the optimal contrast.

The calculating function 204 calculates setting information of an injector that injects the contrast agent into the subject based on the concentration of a contrast agent determined by the determining function 203.

Specifically, the calculating function 204 calculates an injection condition to be set to the injector. AS the setting information of the injector, the calculating function 204 calculates at least one of an injection speed of a contrast agent to be injected to the subject, and a dilution ratio of the contrast agent. For example, the calculating function 204 calculates the setting information based on a relational expression below.

Concentration of Contrast Agent (mg/ml)= $C$*Concentration of Undiluted Contrast Agent (mg/ml)*Injection Speed (ml/s)/Dilution Ratio/ Blood Vessel Diameter 2 (mm2)/Blood Flow (mm/s)

C is a dimensionless coefficient. The concentration of a contrast agent in a blood vessel is related to various parameters. As one example, according to a distance between a position of a blood vessel subject to contrast-enhanced imaging in a region of interest and a position of a distal end of a catheter from which the contrast agent is jetted out, the concentration of the contrast agent at the position of the blood vessel subject to contrast-enhanced imaging changes. Moreover, the blood flow significantly differs between a speed soon after pumped out from an artery near the heart and a speed in a peripheral blood vessel. That is, the blood flow differs depending on a position of the region of interest. Accordingly, it is considered that C and the blood flow are experimentally acquired in advance as functions of a blood vessel diameter.

The calculating function 204 calculates an injection speed and a dilution ratio by applying the concentration of a contrast agent determined by the determining function 203, a concentration of an undiluted solution of a contrast agent to be used for contrast-enhanced imaging, a blood vessel diameter, C, and a blood flow to the relational expression above. For example, when an injector used for the contrast-enhanced imaging has no diluting function, the calculating function 204 calculates the injection speed assuming the dilution ratio as "1.0".

On the other hand, when the injector to be used for contrast-enhanced imaging has diluting function, the calculating function 204 calculates a dilution ratio (or an injection speed), fixing the injection speed (or the dilution ratio) based on a value instructed by the user or set in advance. When the injection speed and the dilution ratio are not fixed, the calculating function 204 calculates the "injection speed (ml/s)/dilution ratio" based on the relational expression above.

As described above, when the setting information of an injector is calculated by the calculating function 204, the control function 202 controls the display 18 to display the setting information. FIG. 3 is a diagram illustrating an example of display information according to the first embodiment. For example, the calculating function 204 calculates an injection speed, setting the dilution ratio to "1.0" or to a fixed value, the control function 202 controls to display, as illustrated in FIG. 3, "CONTRAST AGENT RECOMMENDED CONCENTRATION: 0.4 ml/s" as the injection speed of the contrast agent to be set to the injector. The user can collect a contrast-enhanced image of an optimal contrast by setting the displayed injection speed and the dilution ratio used for calculation of the injection speed to the injector.

The control function 202 can control the display 18 to display information about a part of interest, a blood vessel diameter, a body thickness, a contrast, a concentration of a contrast agent in a blood vessel (mg/ml), a dilution ratio, and the like, in addition to the injection speed of a contrast agent as illustrated in FIG. 3.

Furthermore, the control function 202 can also indicate respective allowable ranges of the injection speed and the dilution ratio when the calculating function 204 calculates the "injection speed (ml/s)/dilution ratio". In such a case, the control function 202 controls the display 18 to display a range of an injection speed possible for the injector, and a dilutable range. The user refers to the displayed range, and specifies a value withing the displayed ranged for one of the injection speed and the dilution ratio. According to the specification by the user, the calculating function 204 calculates a value of the one not specified out of the injection speed and the dilution ratio, and the control function 202 controls to display the calculated value on the display 18.

Figure 4:
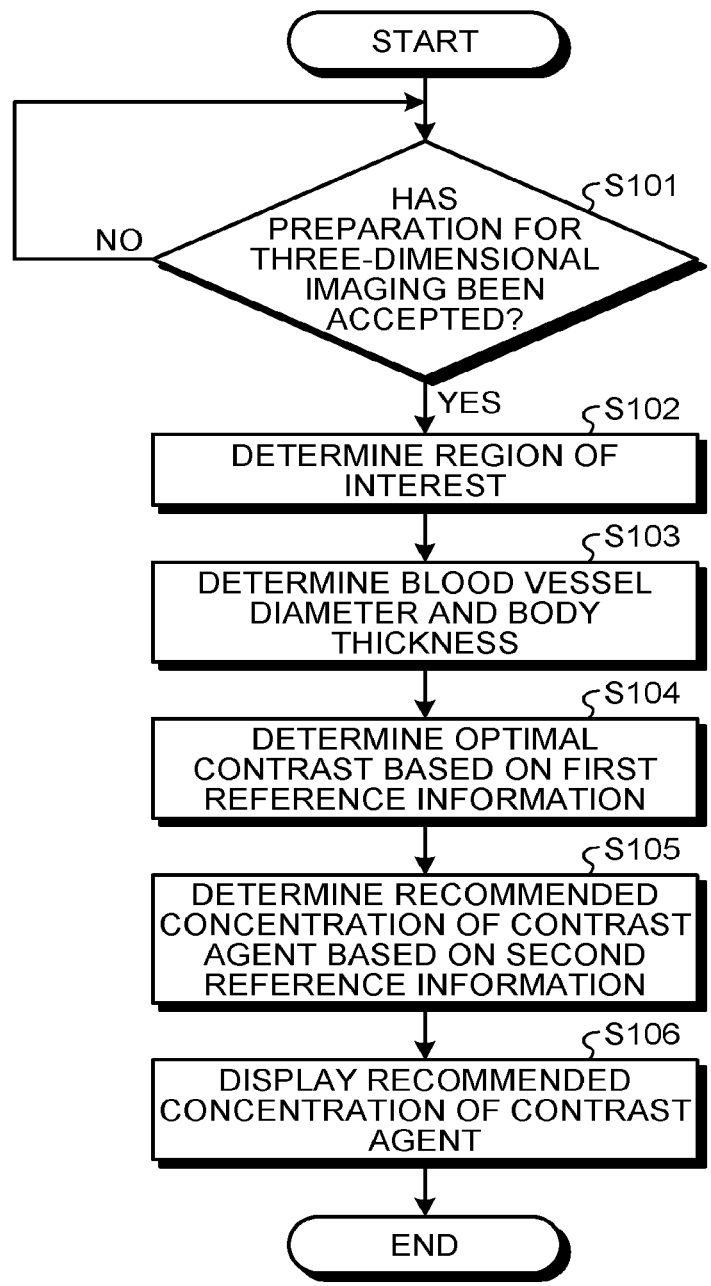
FIG. 4 is a flowchart illustrating a procedure of processing performed by the X-ray diagnostic apparatus according to the first embodiment.

Next, a procedure of the processing performed by the X-ray diagnostic apparatus will be explained. FIG. 4 is a flowchart illustrating a procedure of the processing performed by the X-ray diagnostic apparatus 1 according to the first embodiment. Step S101 to step S104 in FIG. 4 are implemented by reading a program corresponding to the determining function 203 from the memory 17 by the processing circuitry 20, to execute it. Moreover, step S105 is implemented by reading a program corresponding to the calculating function 204 from the memory 17 by the processing circuitry 20, to execute it. Furthermore, step S106 is implemented by reading a program corresponding to the control function 202 from the memory 17 by the processing circuitry 20, to execute it.

As illustrated in FIG. 4, when preparation for three-dimensional contrast-enhanced imaging is accepted (step S101: YES), the processing circuitry 20 determines a region of interest (step S102), and determines a blood vessel diameter and a body thickness in the region of interest (step S103). Note that the processing circuitry 20 waits in a stand-by state until preparation for three-dimensional contrast-enhanced imaging is accepted (step S101: NO).

The processing circuitry 20 then determines an optimal contrast in the region of interest based on the first reference information 171 (step S104). Thereafter, the processing circuitry 20 determines a concentration of a contrast agent in the blood vessel based on the second reference information 172, and calculates a recommended concentration (injection speed) of a contrast agent based on the determined concentration of a contrast agent (step S105). The processing circuitry 20 then controls to display the recommended concentration of a contrast agent on the display (step S106).

As described above, according to the first embodiment, the determining function 203 determines a concentration of a contrast agent in contrast-enhanced image collection based on the first reference information 171 in which a recommended contrast in a contrast-enhanced image is associated with each region of interest subject to contrast-enhanced image collection, and on the second reference information 172 in which a relation among a generation condition of an X-ray, a concentrate of a contrast agent, and a contrast are associated with one another. The calculating function 204 calculates setting information of an injector that injects a contrast agent to a subject based on the determined concentration of a contrast agent. Therefore, the X-ray diagnostic apparatus 1 according to the first embodiment can calculate setting information of an injector to acquire an optimal contrast, and enables easy setting of an injection condition of a contrast agent to acquire a desired contrast without depending on experience.

Moreover, according to the first embodiment, the determining function 203 acquires a recommended contrast in a region of interest of a subject from the first reference information 171, and acquires a concentration of a contrast agent from the second reference information 172 based on the acquired contrast and a generation condition of an X-ray to be irradiated to the subject, to thereby determine a concentration of a contrast agent in contrast-enhanced image collection. Therefore, the X-ray diagnostic apparatus 1 according to the first embodiment enables to determine a concentration of a contrast agent in a blood vessel to acquire an optimal contrast easily.

Furthermore, according to the first embodiment, the first reference information 171 further includes information of a representative blood vessel diameter of each region of interest. The second reference information 172 includes information indicating a relation among a generation condition of an X-ray, a concentration of a contrast agent, and a contrast, for each blood vessel diameter. The determining function 203 determines a blood vessel diameter in a region of interest of a subject based on the first reference information 171, and determines a concentration of a contrast agent in contrast-enhanced image collection based on the second reference information 172 corresponding to the determined blood vessel diameter. Therefore, the X-ray diagnostic apparatus 1 according to the first embodiment can determine a concentration of a contrast agent considering a blood vessel diameter in a region of interest, and enables to set a more accurate injection condition.

Moreover, according to the first embodiment, the first reference information 171 further includes information of a representative body thickness of each region of interest. The second reference information 172 includes information indicating a relation among a generation condition of an X-ray, a concentration of a contrast agent, and a contrast for each body thickness. The determining function 203 determines a body thickness in a region of interest of a subject based on the first reference information 171, and determines a concentration of a contrast agent in contrast-enhanced image collection based on the second reference information 172 corresponding to the determined body thickness. Therefore, the X-ray diagnostic apparatus 1 according to the first embodiment can determine a concentration of a contrast agent considering a body thickness in the region of interest, and enables to set a more accurate injection condition.

Furthermore, according to the first embodiment, the second reference information 172 includes information indicating a relation among a generation condition of an X-ray, a concentration of a contrast agent, and a contrast of each body thickness. The determining function 203 determines a body thickness in a region of interest of a subject from a past image in the region of interest of the subject, and determines a concentration of a contrast agent in contrast-enhanced image collection based on the second reference information 172 corresponding to the determined body thickness. Therefore, the X-ray diagnostic apparatus 1 according to the first embodiment can acquire information of the subject about a body thickness in a region of interest, and enables to set a further accurate injection condition.

Moreover, according to the first embodiment, the setting information is at least one of an injection speed of a contrast agent injected to a subject and a dilution ratio of the contrast agent. Therefore, the X-ray diagnostic apparatus 1 according to the first embodiment can display information to be set to an injector, and enables to set an injection condition easily.

Furthermore, according to the first embodiment, the determining function 203 determines a part of interest in a subject based on an imaging protocol of the subject. Moreover, the determining function 203 determines a part of interest in the subject based on an angle of view size at the time of imaging. Therefore, the X-ray diagnostic apparatus 1 according to the first embodiment enables to accurately identify a region of interest of a subject.

Moreover, according to the first embodiment, the control function 202 controls to display setting information on the display 18. Therefore, the X-ray diagnostic apparatus 1 according to the first embodiment can present setting information of an injector to acquire an optimal contrast to a user, and enables easy setting of an injection condition of a contrast agent to acquire a desired contrast without depending on experience.

Second Embodiment

Figure 5:
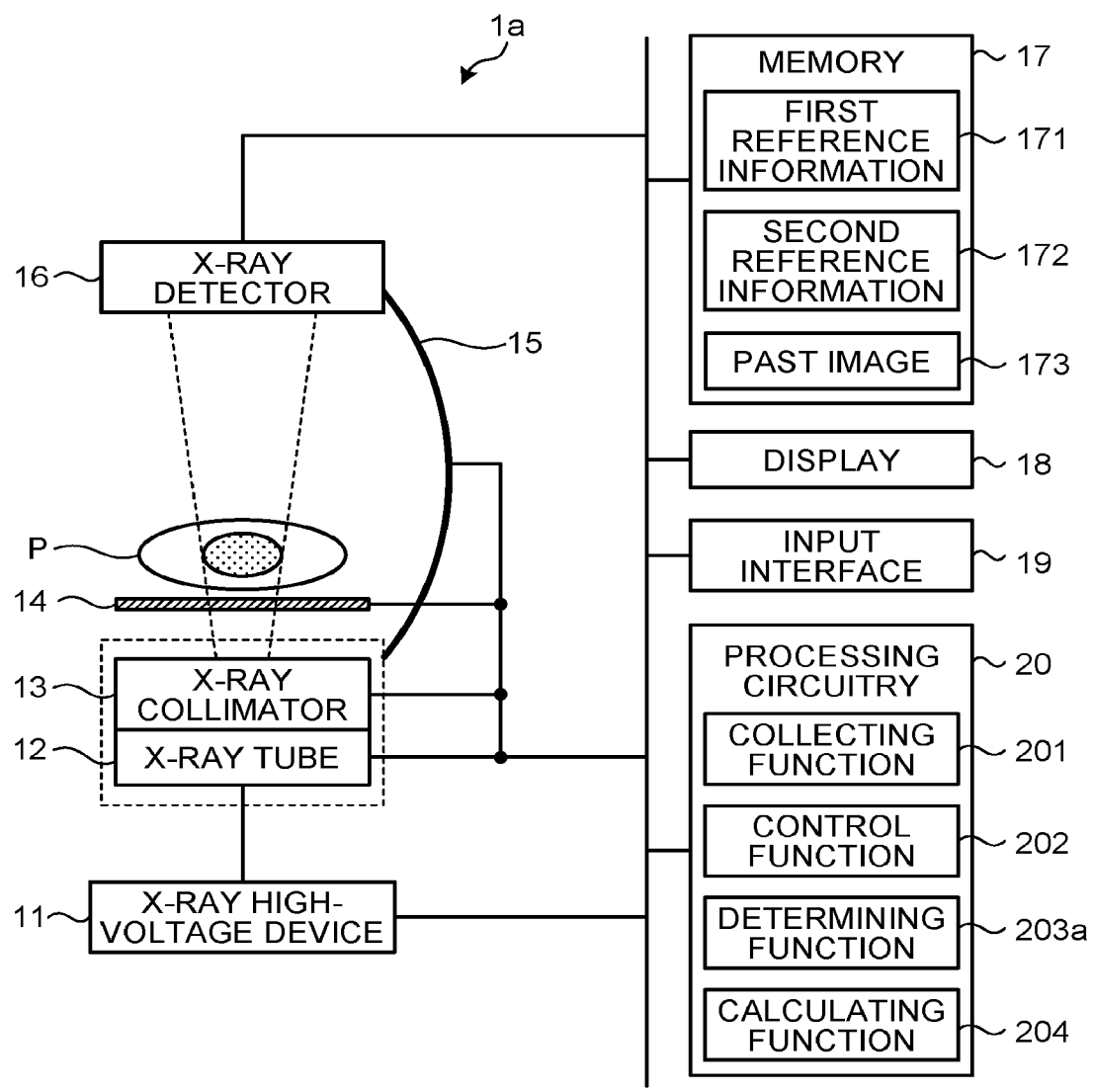
FIG. 5 is a block diagram illustrating an example of a configuration of an X-ray diagnostic apparatus according to a second embodiment.

In the first embodiment described above, a case in which an injection condition of a contrast agent is calculated by using a representative blood vessel diameter that is associated with a region of interest in the first reference information 171 has been explained. In a second embodiment, a case in which a blood vessel diameter of a blood vessel in a region of interest is determined by using a past image of a subject will be explained. FIG. 5 is a block diagram illustrating an example of a configuration of an X-ray diagnostic apparatus 1a according to the second embodiment. The X-ray diagnostic apparatus 1a differs in a point in which a past image is stored in the memory 17, and processing performed by a determining function 203a from the X-ray diagnostic apparatus 1 according to the first embodiment. Hereinafter, these points will be mainly explained.

As illustrated in FIG. 15, the memory 17 according to the second embodiment stores a past image 173. The past image 173 includes a contrast-enhanced image of a subject taken in past. Specifically, the past image 173 includes a contrast-enhanced image acquired by past contrast-enhanced imaging of a region of interest to be a subject to contrast-enhanced imaging of a present time of the subject.

The determining function 203a according to the second embodiment determines a blood vessel diameter in the region of interest of the subject from the past image of the region of interest of the subject, and determines a concentration of a contrast agent in the region of interest of the subject at the time of contrast-enhanced image collection, based on the second reference information 172 corresponding to the determined blood vessel diameter. For example, the determining function 203a acquires a contrast-enhanced image acquired by past contrast-enhanced imaging of the region of interest subject to contrast-enhanced imaging of the present time of the subject from the memory 17, and extracts a blood vessel rendered in the acquired contrast-enhanced image. For this extraction of a blood vessel, any method, such as an existing pattern recognition technique and a blood-vessel-outline extraction technique, can be used.

The determining function 203a extracts a blood vessel in the contrast-enhanced image by a technique as described above, and converts a blood vessel diameter of the extracted blood vessel into an actual blood vessel diameter. For example, similarly to a case of measuring length in an image, calibration to correspond length on the table and length in the image is performed in advance. The determining function 203a converts the blood vessel diameter of the blood vessel in the contrast-enhanced image into an actual blood vessel diameter based on information of the calibration.

As described above, having acquired the blood vessel diameter from the past image, the determining function 203a determines a concentration of a contrast agent in the region of interest of the subject at the time of contrast-enhanced image collection based on the second reference information 172 corresponding to the acquired blood vessel diameter.

As described above, according to the second embodiment, the second reference information 172 includes information indicating a relation among a generation condition of an X-ray, a concentration of a contrast agent, and a contrast of each blood vessel diameter. The determining function 203a determines a blood vessel diameter in a region of interest of a subject from a past image of the region of interest of the subject, and determines concentration of a contrast agent in the region of interest of the subject at the time of contrast-enhanced image collection based on the second reference information 172 corresponding to the determined blood vessel diameter. Therefore, the X-ray diagnostic apparatus 1a according to the second embodiment can acquire an actual blood vessel diameter of a blood vessel subject to contrast-enhanced imaging, and enables to set a more accurate injection condition.

Third Embodiment

Figure 6:
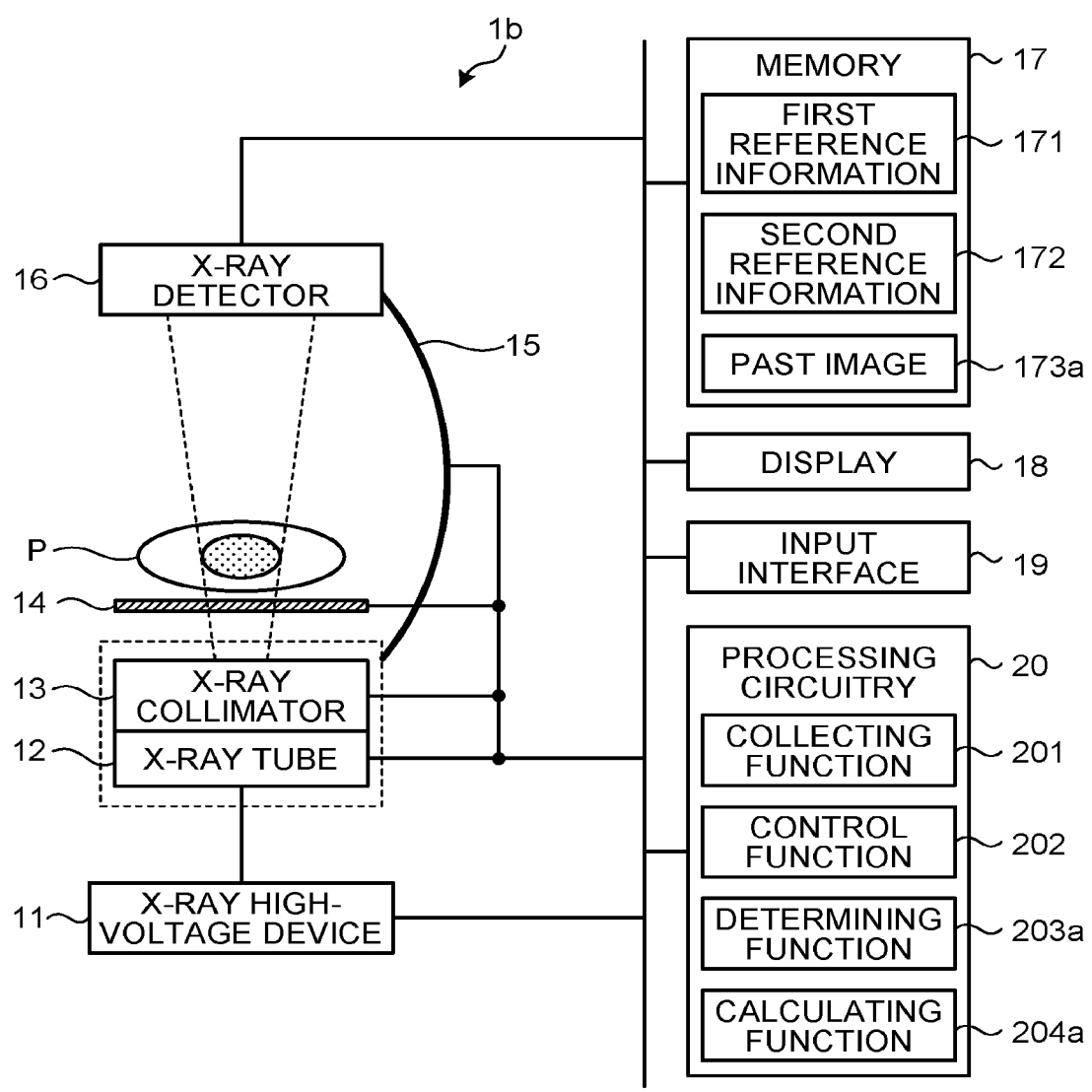
FIG. 6 is a block diagram illustrating an example of a configuration of an X-ray diagnostic apparatus according to a third embodiment.

In the second embodiment described above, a case in which an actual blood vessel diameter is acquired by using a past contrast-enhanced image of a subject has been explained. In a third embodiment, a case in which an injection condition of a contrast agent is further associated with a past image of a subject, and the setting information is corrected by using a result of past contrast-enhanced imaging will be explained. FIG. 6 is a block diagram illustrating an example of a configuration of an X-ray diagnostic apparatus 1b according to the third embodiment. The X-ray diagnostic apparatus 1b according to the third embodiment differs in information stored in the memory 17, and processing performed by a calculating function 204a from the X-ray diagnostic apparatus 1a according to the second embodiment. Hereinafter, these points will be mainly explained.

A past image 173a according to the third embodiment is information in which an injection condition of a contrast agent is associated with a contrast-enhanced image that is taken in past by contrast-enhanced imaging a region of interest subject to contrast-enhanced imaging of a present time of a subject. For example, in the past image 173a, a past contrast-enhanced image, an injection speed and a dilution ratio of a contrast agent that are set to an injector when the contrast-enhanced image was collected, and a generation condition of an X-ray when the contrast-enhanced image was collected are associated with one another.

The calculating function 204a according to the third embodiment corrects setting information based on a contrast of the past contrast-enhanced image of the region of interest of the subject, and on the setting information of the injector at the time of collection of the contrast-enhanced image. Specifically, first, the calculating function 204a calculates a contrast of a blood vessel in the past contrast-enhanced image extracted by the determining function 203a. For example, the calculating function 204a calculates a contrast of a blood vessel in the past contrast-enhanced image by calculating pixel value of contrast-enhanced blood vessel/ pixel value of periphery of the blood vessel.

The calculating function 204a calculates a correction coefficient by comparing setting information that has been calculated by applying the concentration of a contrast agent determined by the determining function 203a, a concentration of an undiluted contrast agent to be used for contrast-enhanced imaging, a blood vessel diameter, C, and a blood flow to the relational expression described above, with the setting information of the past image.

For example, it is supposed that a contrast of a blood vessel in a past image that was taken by contrast-enhanced imaging a region of interest of "BODY THICKNESS: 20 cm" AND "BLOOD VESSEL DIAMETER: 2.0 cm" with "X-RAY TUBE VOLTAGE: 70 kV", "INJECTION SPEED OF CONTRAST AGENT: 10 ml/s", and "DILUTION RATIO OF CONTRAST AGENT: 1.0" is "2.0". On the other hand, it is assumed that a result of calculation for an injection speed of a contrast agent when imaging with the same generation condition of an X-ray and the same contrast based on the concentration of a contrast agent determined by the determining function 203a is "15 ml/s".

In this case, the calculating function 204a compares the "INJECTION SPEED OF CONTRAST AGENT: 10 ml" of the past image and the "INJECTION SPEED OF CONTRAST AGENT: 15 ml/s" calculated based on the current concentration of a contrast agent in the second reference information 172, and estimates that the calculated injection speed of a contrast agent is calculated as a larger value than the actual injection speed.

Moreover, when the first reference information 171 is referred about an optimal contrast for a region of interest having the "BODY THICKNESS: 20 cm" and "BLOOD VESSEL DIAMETER: 2.0 cm" and it is "3.0", and when the injection speed to obtain the contrast of "3.0" is "20 ml/s", the calculating function 204a estimates that this injection speed is also calculated as a larger value than the actual injection speed.

As described, when there is a difference between the calculated injection speed and the actual injection speed, the calculating function 204a calculates a correction coefficient to correct the calculated injection speed based on the actual injection speed. For example, when there is a difference as described above, the calculating function 204a calculates a correction coefficient "10/15", and calculates "20*10/15=13.3" as an injection speed after correction.

In the above example, a case in which a ratio of an injection speed to an actual injection speed "10/15" based on the second reference information 172 is used as the correction coefficient has been explained. However, the correction coefficient is not limited thereto and, for example, the correction coefficient may be f(10/15) using the function f in the above ratio. In this case, the injection speed after correction will be "20*f(10/15)".

Figure 7:
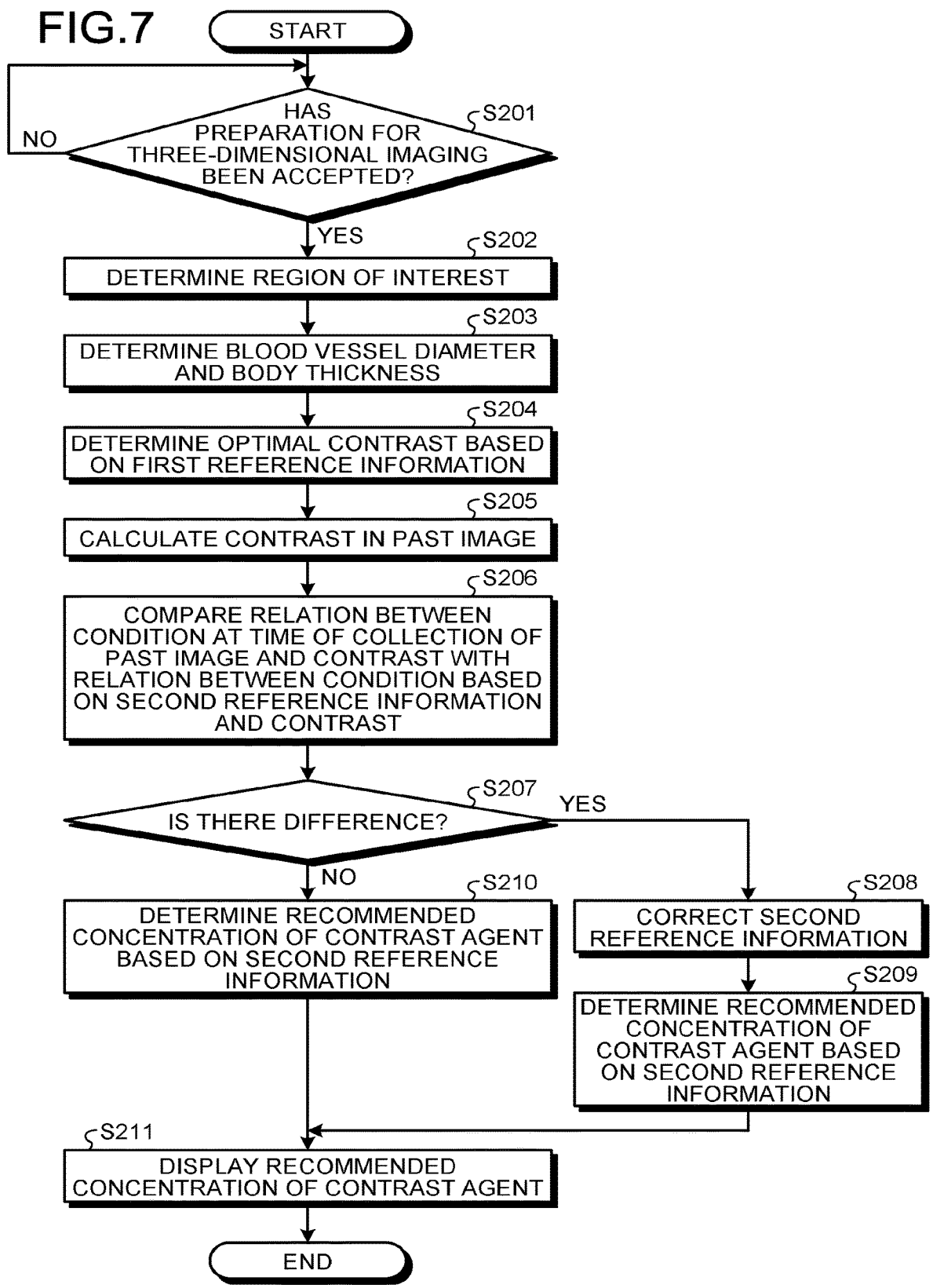
FIG. 7 is a flowchart illustrating a procedure of processing performed by the X-ray diagnostic apparatus according to the third embodiment.

Next, a procedure of the processing performed by the X-ray diagnostic apparatus according to the third embodiment will be explained. FIG. 7 is a flowchart illustrating a procedure of the processing performed by the X-ray diagnostic apparatus 1b according to the third embodiment. Step S201 to step S204 in FIG. 7 are implemented by reading a program corresponding to the determining function 203a from the memory 17 by the processing circuitry 20, to execute it. Moreover, step S205 to step S210 are implemented by reading a program corresponding to the calculating function 204a from the memory 17 by the processing circuitry 20, to execute it. Furthermore, step S211 is implemented by reading a program corresponding to the control function 202 from the memory 17 by the processing circuitry 20, to execute it.

As illustrated in FIG. 7, when preparation for three-dimensional contrast-enhanced imaging is accepted (step S201: YES), the processing circuitry 20 determines a region of interest (step S202), and determines a blood vessel diameter and a body thickness in the region of interest (step S203). Note that the processing circuitry 20 waits in a stand-by state until preparation for three-dimensional contrast-enhanced imaging is accepted (step S201: NO).

The processing circuitry 20 then determines an optimal contrast in the region of interest based on the first reference information 171 (step S204). Thereafter, the processing circuitry 20 calculates a contrast in a past image (step S205), and compares a relation between the condition at the time of collecting the past image and its contrast and a relation between a condition based on the second reference information 172 and a contrast (step S206), to determine whether there is a difference therebetween (step S207).

When there is a difference (step S207: YES), the processing circuitry 20 calculates a correction coefficient to correct the second reference information 172 (step S208), and determines a recommended concentration (injection speed) of a contrast agent by using the correction coefficient (step S209). On the other hand, when it is determined at step S207 that there is no difference (step S207: NO), the processing circuitry 20 determines a recommended concentration (injection speed) of a contrast agent based on the second reference information 172 (step S210). The processing circuitry 20 displays the recommended concentration of a contrast agent on the display 18 (step S211).

As described above, according to the third embodiment, the calculating function 204a corrects setting information based on a contrast of a past contrast-enhanced image of a region of interest of a subject and on setting information of an injector at the time of collecting the contrast-enhanced image. Therefore, the X-ray diagnostic apparatus 1b according to the third embodiment can feedback a result of past contrast-enhanced imaging, and enables to set a more accurate injection condition of a contrast agent easily without depending on experience.

Fourth Embodiment

Figure 8:
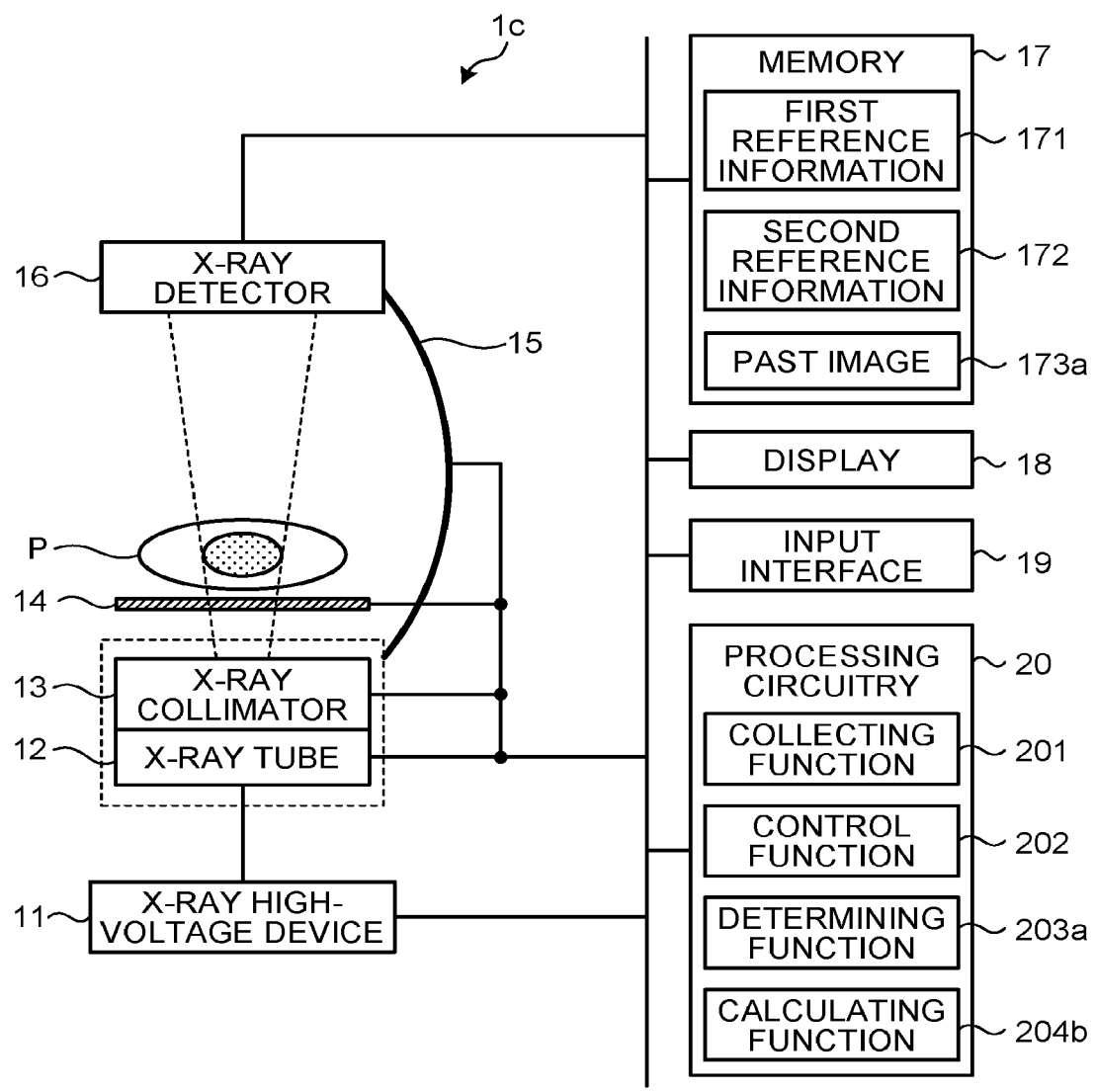
FIG. 8 is a block diagram illustrating an example of a configuration of an X-ray diagnostic apparatus according to a fourth embodiment.

In the third embodiment described above, a case in which correction is performed by comparing an injection condition in a past contrast-enhanced image and an injection condition calculated at a present time has been explained. In a fourth embodiment, a case in which setting information is corrected based on a past three-dimensional blood-vessel image will be explained. FIG. 8 is a block diagram illustrating an example of a configuration of an X-ray diagnostic apparatus 1c according to the fourth embodiment. The X-ray diagnostic apparatus 1c according to the fourth embodiment differs in processing performed by a calculating function 204b from the X-ray diagnostic apparatus 1b according to the third embodiment. Hereinafter, this point will be mainly explained.

The past image 173a according to the fourth embodiment includes a contrast-enhanced image acquired by past contrast-enhanced imaging of a region of interest to be a subject to contrast-enhanced imaging of a present time of the subject. Specifically, the past image 173a includes three-dimensional blood-vessel image data that is reconstructed based on projection data collected by rotational imaging. For example, the past image 173a includes three-dimensional blood-vessel image data collected before operation.

The calculating function 204b according to the fourth embodiment corrects setting information by using the three-dimensional blood-vessel image data. Specifically, the calculating function 204b corrects the setting information based on an artifact included in past three-dimensional blood-vessel image data of a region of interest of the subject.

For example, when a contrast of a blood vessel is too high in a blood vessel contrast-enhanced image that is used for reconstruction of three-dimensional blood-vessel image data, a voxel value (CT value) of the blood vessel in reconstructed three-dimensional blood-vessel image data is to be too high, and a radial artifact can occur. Accordingly, the calculating function 204b corrects the setting information based on the quality of blood vessel rendition in past three-dimensional blood-vessel image data. That is, the calculating function 204b performs following correction when an artifact is caused in the past three-dimensional blood-vessel image data.

In such a case, the calculating function 204b acquires a voxel value of a blood vessel in the past three-dimensional blood-vessel image data, and calculates a ratio of the acquired voxel value to a target voxel value. As the voxel value of the blood vessel, a voxel value specified by a user, or a voxel value corresponding to the blood vessel extracted based on an existing algorithm from the past three-dimensional blood-vessel image data is acquired.

Moreover, the target voxel value may be a voxel value set the user when observing the past three-dimensional blood-vessel image data, or a value set in advance may be used. When a target value is set in advance, it may be configured such that the target voxel value in three-dimensional blood-vessel image data is further associated with the first reference information 171.

As described above, having calculated a ratio of the voxel values, the calculating function 204b corrects a contrast of a contrast-enhanced image of the blood vessel by using the calculated ratio as the correction coefficient, and calculates an injection condition of a contrast agent so as to obtain a corrected contrast.

Figure 9:
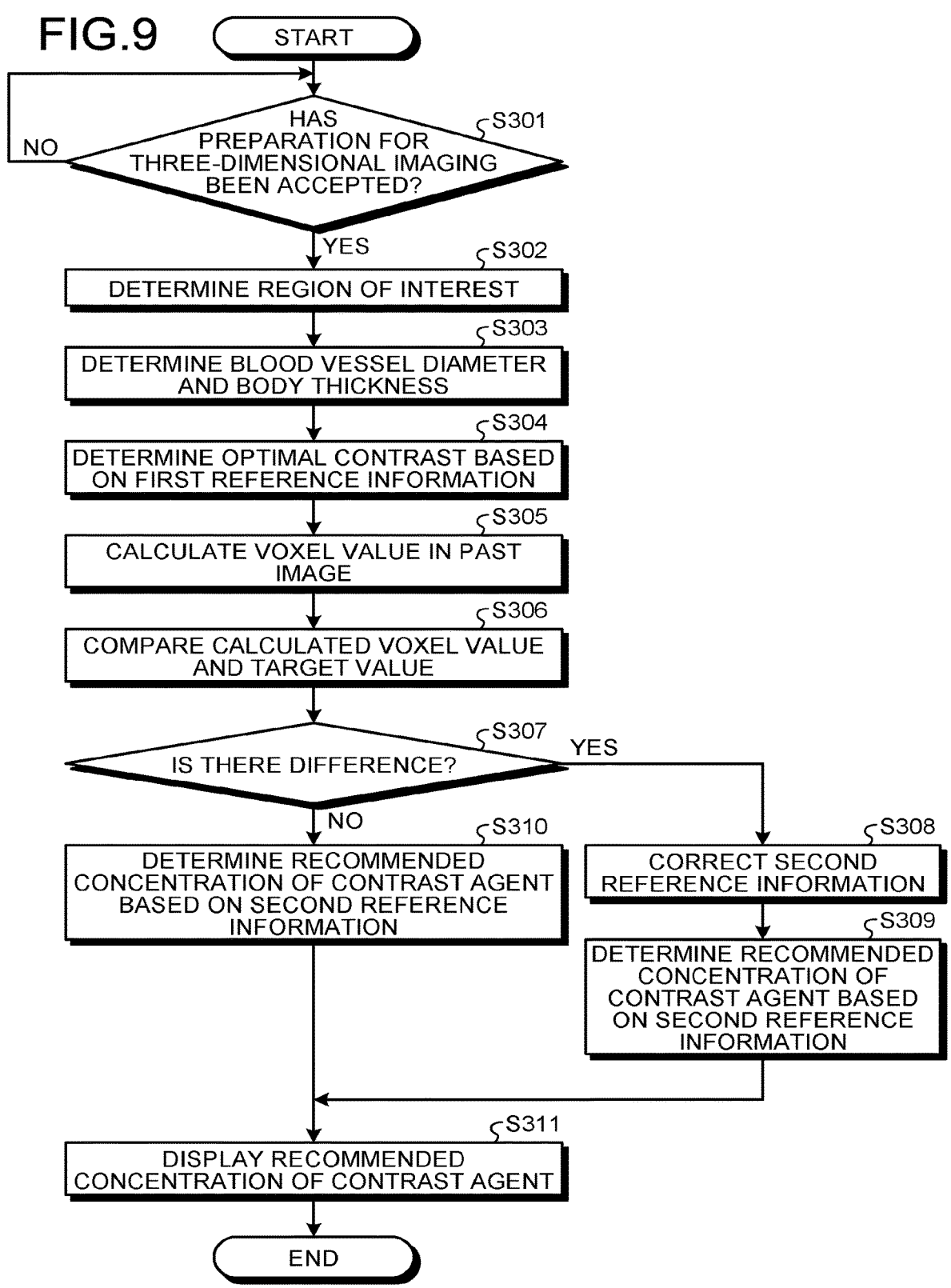
FIG. 9 is a flowchart illustrating a procedure of processing performed by the X-ray diagnostic apparatus according to the fourth embodiment.

Next, a procedure of processing performed by the X-ray diagnostic apparatus 1c according to the fourth embodiment will be explained. FIG. 9 is a flowchart illustrating a procedure of the processing performed by the X-ray diagnostic apparatus 1c according to the fourth embodiment. Step S301 to step S304 in FIG. 9 are implemented by reading a program corresponding to the determining function 203a from the memory 17 by the processing circuitry 20, to execute it. Moreover, step S305 to step S310 are implemented by reading a program corresponding to the calculating function 204b from the memory 17 by the processing circuitry 20, to execute it. Furthermore, step S311 is implemented by reading a program corresponding to the control function 202 from the memory 17 by the processing circuitry 20, to execute it.

As illustrated in FIG. 9, when preparation for three-dimensional contrast-enhanced imaging is accepted (step S301: YES), the processing circuitry 20 determines a region of interest (step S302), and determines a blood vessel diameter and a body thickness in the region of interest (step S303). Note that the processing circuitry 20 waits in a stand-by state until preparation for three-dimensional contrast-enhanced imaging is accepted (step S301: NO).

The processing circuitry 20 then determines an optimal contrast in the region of interest based on the first reference information 171 (step S304). Thereafter, the processing circuitry 20 calculates a voxel value in a past image (step S305), and compares the calculated voxel value and a target value (step S306), to determine whether there is a difference therebetween (step S307).

When there is a difference (step S307: YES), the processing circuitry 20 calculates a correction coefficient to correct the second reference information 172 (step S308), and determines a recommended concentration (injection speed) of a contrast agent by using the correction coefficient (step S309). On the other hand, when it is determined at step S307 that there is no difference (step S307: NO), the processing circuitry 20 determines a recommended concentration (injection speed) of a contrast agent based on the second reference information 172 (step S310). The processing circuitry 20 displays the recommended concentration of a contrast agent on the display 18 (step S311).

As described above, according to the fourth embodiment, the calculating function 204a corrects the setting information based on an artifact included in past contrast-enhanced three-dimensional image of a region of interest of a subject. Therefore, X-ray diagnostic apparatus 1c according to the fourth embodiment can feedback a result of three-dimensional blood-vessel image, and enables to set a more accurate injection condition of a contrast agent easily without depending on experience.

Fifth Embodiment

Figure 10:
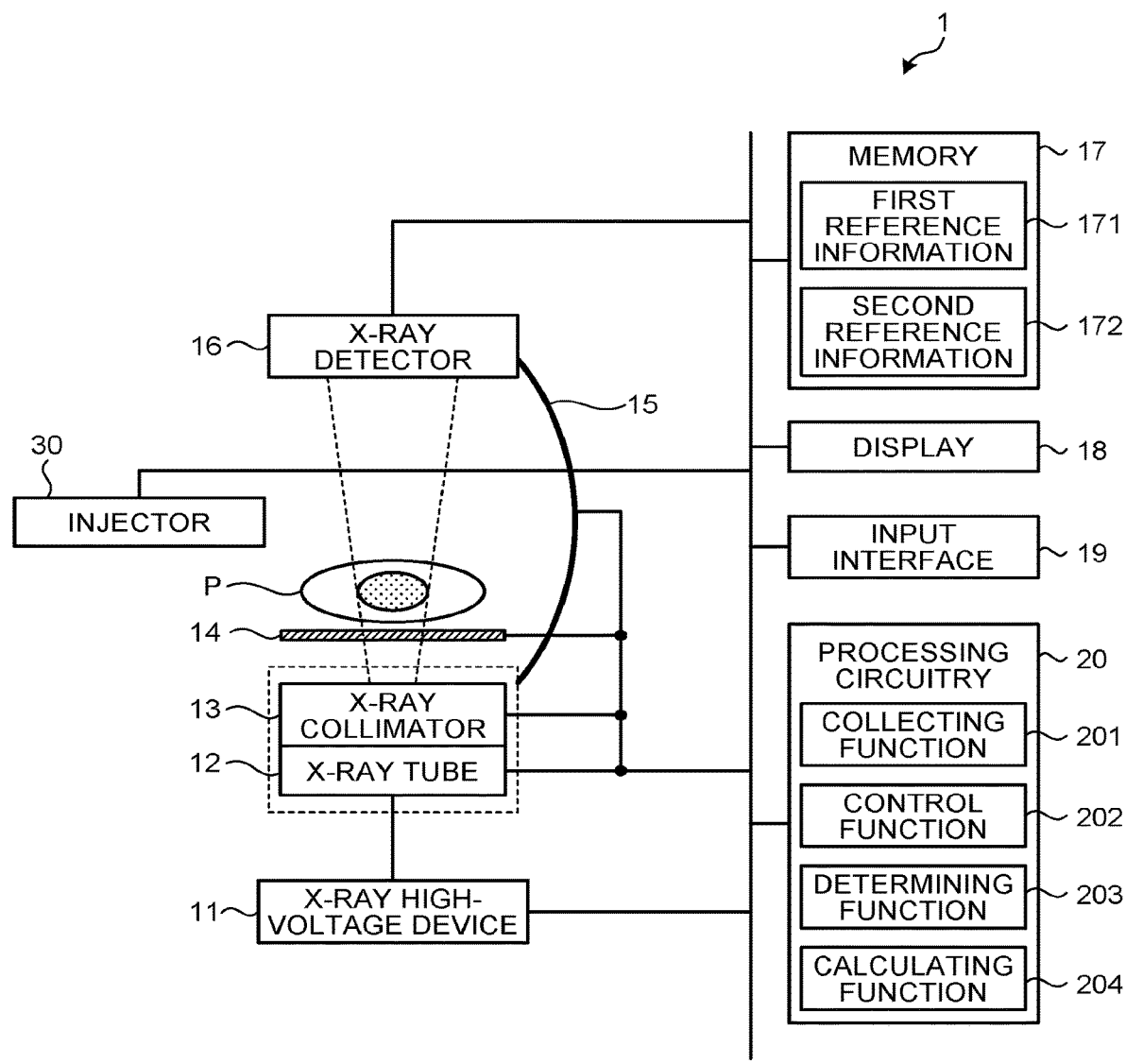
FIG. 10 is a block diagram illustrating an example of a configuration of an X-ray diagnostic apparatus according to a fifth embodiment.

In the first embodiment described above, a case in which the calculated setting information is displayed on the display 18 has been explained. In a fifth embodiment, the calculated setting information is transmitted, to an injector to control the injector will be explained. FIG. 10 is a block diagram illustrating an example of a configuration of the X-ray diagnostic apparatus 1 according to the fifth embodiment. The X-ray diagnostic apparatus 1 according to the fifth embodiment differs in a point in which an injector 30 is connected, and in processing performed by the control function 202, from the X-ray diagnostic apparatus 1 according to the first embodiment. Hereinafter, these will be mainly explained.

As illustrated in FIG. 10, to the X-ray diagnostic apparatus 1 according to the fifth embodiment, the injector 30 is connected. The injector 30 includes an interface to externally control start and stop of injection. Moreover, the injector 30 includes an interface to externally set an injection condition of a contrast agent (an injection speed of a contrast agent, a dilution ratio, and the like). A processing circuit in the injector 30 receives setting information or a start instruction and a stop instruction of injection from the X-ray diagnostic apparatus 1 through the interface described above. The injector 30 sets the received setting information to its own device, and starts and stops injection of a contrast agent in accordance with the start instruction and the stop instruction of injection.

The control function 202 according to the fifth embodiment transmits the setting information calculated by the calculating function 204 to the injector 30.

Specifically, the control function 202 causes the injector 30 to set the injection condition by transmitting the injection condition of a contrast agent calculated by the calculating function 204. The control function 202 transmits setting information including at least one of a total amount of a contrast agent, injection time, and an injection start timing to the injector 30. The control function 202 can cause the display 18 to display the injection condition, in addition to transmitting the injection condition to the injector 30.

Moreover, the control function 202 transmits a start instruction and a stop instruction to the injector 30 based on a start timing, imaging time, and an end timing of three-dimensional contrast-enhanced imaging. For example, when three-dimensional blood-vessel image data is collected, an injected state of a contrast agent in a subject blood vessel is necessary to be in a uniform state at respective angles in rotational imaging. Therefore, the control function 202 determines a start timing and an end timing of injection based on the start timing, the imaging time, and the end timing of three-dimensional contrast-enhanced imaging, and informs of the determined start timing and end timing to the injector 30. The start timing of injection is informed predetermined time before the start timing of three-dimensional contrast-enhanced imaging.

Although a case in which the injector 30 is connected to the X-ray diagnostic apparatus 1 according to the first embodiment is illustrated in FIG. 10, the injector 30 may be connected to any of the X-ray diagnostic apparatuses in the second to the fourth embodiments. In such a case, the X-ray diagnostic apparatuses according to the respective embodiments transmit the injection condition, or the start instruction and the stop instruction to the injector 30.

Furthermore, injection of a contrast agent by the injector is controlled by transmitting the injection condition to the injector 30, the injection condition may be changed in real time while collecting contrast-enhanced images. For example, injection of a contrast agent by the injector 30 may be changed in real time by performing the correction of an injection condition using a collected contrast-enhanced image explained in the third embodiment in real time, and by transmitting the corrected injection condition to the injector 30.

Next, a procedure of processing performed by the X-ray diagnostic apparatus will be explained. FIG. 11 is a flowchart illustrating a procedure of processing performed by the X-ray diagnostic apparatus 1 according to the fifth embodiment. Step S401 to step S404 in FIG. 11 are implemented by reading a program corresponding to the determining function 203 from the memory 17 by the processing circuitry 20, to execute it. Moreover, step S405 is implemented by reading a program corresponding to the calculating function 204 from the memory 17 by the processing circuitry 20, to execute it. Furthermore, step S406 to step S408 are implemented by reading a program corresponding to the control function 202 from the memory 17 by the processing circuitry 20, to execute it.

As illustrated in FIG. 11, when preparation for three-dimensional contrast-enhanced imaging is accepted (step S401: YES), the processing circuitry 20 determines a region of interest (step S402), and determines a blood vessel diameter and a body thickness in the region of interest (step S403). Note that the processing circuitry 20 waits in a stand-by state until preparation for three-dimensional contrast-enhanced imaging is accepted (step S401: NO).

The processing circuitry 20 then determines an optimal contrast in the region of interest based on the first reference information 171 (step S404). Thereafter, the processing circuitry 20 determines a concentration of a contrast agent in a blood vessel based on the second reference information 172, and calculates a recommended concentration (injection speed) of a contrast agent based on the determined concentration of a contrast agent (step S405). The processing circuitry 20 displays the recommended concentration of a contrast agent on the display 18 (step S406), and transmits setting information to the injector 30 (step S407). Furthermore, the processing circuitry 20 transmits a start instruction and an end instruction of injection to the injector 30, to control start and end of injection (step S408).

As described above, according to the fifth embodiment, the control function 202 transmits calculated setting information to the injector 30. Moreover, the control function 202 transmits the setting information further including at least one of a total amount of a contrast agent, injection time, and an injection start timing, to the injector 30. Therefore, the X-ray diagnostic apparatus 1 according to the fifth embodiment enables to perform setting of an injection condition of a contrast agent and control of an injector automatically.

OTHER EMBODIMENTS

The first to the fifth embodiments have so far been explained, but it may be implemented by various different forms other than the first to the fifth embodiments described above.

In the embodiments described above, a case in which various kinds of processing are performed by an X-ray diagnostic apparatus has been explained. However, embodiments are not limited thereto, and the respective processing described above may be performed by a medical-information processing apparatus.

FIG. 12 is a block diagram illustrating an example of a configuration of a medical-information processing apparatus 3 according to another embodiment. As illustrated in FIG. 12, the medical-information processing apparatus 3 is connected to the X-ray diagnostic apparatus 1 through a network 2. The medical-information processing apparatus 3 includes a communication interface 31, a memory 32, an input interface 33, a display 34, and processing circuitry 35. The medical-information processing apparatus 3 is an information processing apparatus, such as a tablet terminal and a workstation.

The communication interface 31 is connected to the processing circuitry 35, and transmission and communication of various kinds of data performed with respect to the X-ray diagnostic apparatus 1 connected through the network and the like are controlled. For example, the communication interface 31 is implemented by a network card, a network adaptor, a network interface controller (NIC), and the like.

The memory 32 is connected to the processing circuitry 35, and stores various kinds of data. For example, the memory 32 is implemented by a semiconductor memory device, such as a random access memory (RAM) and a flash memory, a hard disk, an optical disk, and the like. In the present embodiment, the memory 32 stores a medical image (past image 173) received from the X-ray diagnostic apparatus, the first reference information 171, and the second reference information 172. Furthermore, the memory 32 stores various kinds of information used for processing by the processing circuitry 35, a processing result by the processing circuitry 35, and the like.

The input interface 33 is implemented by a trackball, a switch button, a mouse, a keyboard, a touchpad with which an input operation is performed by touching an operating surface, a touch monitor in which a display screen and a touchpad are integrated, a non-contact input circuit using an optical sensor, a voice input circuit, and the like to perform various configurations. The input interface 33 is connected to the processing circuitry 35, and converts an input operation accepted from an operator into an electrical signal, to output it to the processing circuitry 35. In the present application, the input interface 33 is not limited to one that includes a physical operating part, such as a mouse and a keyboard. For example, a processing circuit that receives an electrical signal corresponding to an input operation from an external input device that is provided separately from the apparatus, and that outputs this electrical signal to the control circuit is also included in examples of the input interface.

The display 34 is connected to the processing circuitry 35, and displays various kinds of information and various kinds of images output from the processing circuitry 35. For example, the display 34 is implemented by a liquid crystal monitor, a cathode ray tube (CRT) monitor, a touch monitor, or the like. For example, the display 34 displays a user interface (UI) to receive an instruction of an operator, various kinds of images, and various processing results (setting information) obtained by the processing circuitry 35.

The processing circuitry 35 controls various components included in the medical-information processing apparatus 3 in accordance with an input operation received from the operator through the input interface 33. The processing circuitry 35 performs, for example, a control function 351, a determining function 352, and a calculating function 353 as illustrated in FIG. 12. For example, the respective processing functions performed by the control function 351, the determining function 352, and the calculating function 353, which are components of the processing circuitry 35 illustrated in FIG. 12 are recorded in the memory 32 in a form of a computer-executable program. The processing circuitry 35 is, for example, a processor, and reads and executes respective programs from the memory 32, and thereby implements functions corresponding to the read respective programs. In other words, the processing circuitry 35 that has read the respective programs is to have the respective functions indicated in the processing circuitry 35 in FIG. 12.

The control function 351 overall controls the medical-information processing apparatus 3. Furthermore, the control function 351 performs processing similar to that of the control function 202 described above. The determining function 352 performs processing similar to that of the determining functions 203, 203a described above. The calculating function 353 performs processing similar to that of the calculating functions 204, 204a, 204b described above.

In the X-ray diagnostic apparatus explained in the respective embodiments, the respective processing functions are stored in the memory 17 in a form of a computer-executable program. The processing circuitry 20 is a processor that reads and executes the program from the memory 17, to implement functions corresponding to the respective programs. In other words, the processing circuitry 20 that has read the respective programs is to have functions corresponding to the read respective programs. In the respective embodiments described above, a case in which the respective processing functions are implemented by a single unit of the processing circuitry 20 has been described, but embodiments are not limited thereto. For example, the processing circuitry 20 may be configured by combining plural independent processors, and it may be configured such that the respective processing functions are implemented by executing the respective programs by the respective processors. Moreover, the respective processing functions included in the processing circuitry 20 may be implemented by appropriately distributing to or integrating in a single unit of or plural units of the processing circuits.

A term "processor" used in the above explanation signifies a circuit, such as a central processing unit (CPU), a graphical processing unit (GPU), an application specific integrated circuit (ASIC), a programmable logic device (for example, simple programmable logic device (SPL), complex programmable logic device (CPLD)), and a field programmable gate array (FPGA). The processor implements a function by reading and executing a program stored in a storage 111.

In the respective embodiments described above, it has been explained that the memory 17 stores programs corresponding to the respective functions. However, plural units of the memory 17 may be arranged in a distributed manner, and the processing circuitry 20 may be configured to read a corresponding program from an individual unit of the memory 17. Moreover, instead of storing a program in the memory 17, it may be configured to directly install a program in a circuit of the processor. In this case, the processor reads and executes the program installed in the circuit, to implement the function.

The respective components of the respective devices according to the embodiments described above are of functional concept, and it is not necessarily required to be configured physically as illustrated. That is, specific forms of distribution and integration of the respective devices are not limited to the ones illustrated, and all or some thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the control method explained in the above embodiments can be implemented by executing a program that has been prepared in advance by a computer such as a personal computer and a workstation. This control program can be distributed through a network such as the Internet. Furthermore, this control program can be recorded on a non-transient recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments explained above, an injection condition of a contrast agent to acquire a desirable contrast can be set easily without depending on experience.

Regarding the above embodiments, following notes are disclosed as one aspect and selective features of the invention.

Note 1

An X-ray diagnostic apparatus comprising processing circuitry that determines a concentration of a contrast agent in contrast-enhanced image collection based on first reference information in which a recommended contrast in a contrast-enhanced image is associated with each region of interest to be subject to collection of the contrast-enhanced image, and on second reference information that indicates a relation among a generation condition of an X-ray, a concentration of a contrast agent, and a contrast, and that calculates setting information of an injector to inject a contrast agent to the subject based on the determined concentration of a contrast agent.

Note 2

The processing circuitry may determine the concentration of a contrast agent in contrast-enhanced image collection by acquiring a recommended contrast for the region of interest of the subject from the first reference information, and by acquiring a concentration of a contrast agent from the second reference information based on the acquired contrast and a generation condition of an X-ray to be irradiated to the subject.

Note 3

The first reference information may further include information of a representative blood vessel diameter of each region of interest, the second reference information may include information indicating a relation among the generation condition of an X-ray, the concentration of a contrast agent, and the contrast for each blood vessel diameter, and the processing circuitry may determine a blood vessel diameter in the region of interest of the subject based on the first reference information, and determine the concentration of a contrast agent in contrast-enhance image collection based on the second reference information corresponding to the determined blood vessel diameter.

Note 4

The first reference information may further include information of a representative body thickness of each region of interest, the second reference information may include information indicating a relation among the generation condition of an X-ray, the concentration of a contrast agent, and the contrast for each body thickness, and the processing circuitry may determine a body thickness in the region of interest of the subject based on the first reference information, and may determine the concentration of a contrast agent in contrast-enhance image collection based on the second reference information corresponding to the determined body thickness.

Note 5

The second reference information may include information indicating a relation among the generation condition of an X-ray, the concentration of a contrast agent, and the contrast for each blood vessel diameter, and the processing circuitry may determine a blood vessel diameter in the region of interest of the subject from a past image of the region of interest of the subject, and may determine the concentration of a contrast agent in contrast-enhance image collection based on the second reference information corresponding to the determined blood vessel diameter.

Note 6

The second reference information may include information indicating a relation among the generation condition of an X-ray, the concentration of a contrast agent, and the contrast for each body thickness, and the processing circuitry may determine a body thickness in the region of interest of the subject from a past image of the region of interest of the subject, and may determine the concentration of a contrast agent in contrast-enhance image collection based on the second reference information corresponding to the determined body thickness.

Note 7

The setting information may be at least one of an injection speed of a contrast agent to be injected to the subject and a dilution ratio of the contrast agent.

Note 8

The processing circuitry may determine a part of interest in the subject based on an imaging protocol of the subject.

Note 9

The processing circuitry may determine a part of interest in the subject based on a size of a field of view at imaging.

Note 10

The processing circuitry may correct the setting information based on a contrast of a past contrast-enhanced image of the region of interest of the subject, and on setting information of an injector at collection of the contrast-enhanced image.

Note 11

The processing circuitry may correct the setting information based on an artifact included in a past three-dimensional contrast-enhanced image of the region of interest of the subject.

Note 12

The processing circuitry may cause a display unit to display the setting information.

Note 13

The processing circuitry may transmit the calculated setting information to the injector.

Note 14

The processing circuitry may transmit setting information further including at least one of a total amount of a contrast agent, injection time, and an injection start timing, to the injector.

Note 15

A medical-information processing apparatus comprising processing circuitry that determines a concentration of a contrast agent in contrast-enhanced image collection based on first reference information in which a recommended contrast in a contrast-enhanced image is associated with each region of interest to be subject to collection of the contrast-enhanced image, and on second reference information that indicates a relation among a generation condition of an X-ray, a concentration of a contrast agent, and a contrast, and that calculates setting information of an injector to inject a contrast agent to the subject based on the determined concentration of a contrast agent.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to
determine, before performing contrast-enhanced imaging, a particular concentration of a contrast agent in a blood vessel included in a contrast-enhanced image to be collected, based on first reference information in which a recommended contrast in a contrast-enhanced image is associated with each region of interest to be subject to collection of the contrast-enhanced image, and on second reference information that indicates a relation among a generation condition of an X-ray, a corresponding concentration of the contrast agent, and a contrast, and
calculate setting information of an injector to inject the contrast agent to the subject based on the determined concentration of the contrast agent.

2. The X-ray diagnostic apparatus according to claim 1, wherein
the processing circuitry is further configured to determine the particular concentration of the contrast agent in the blood vessel included in the contrast-enhanced image to be collected by acquiring a recommended contrast for the region of interest of the subject from the first reference information, and by acquiring the particular concentration of the contrast agent from the second reference information based on the acquired recommended contrast and a particular generation condition of an X-ray to be irradiated to the subject.

3. The X-ray diagnostic apparatus according to claim 1, wherein
the first reference information further includes information of a representative blood vessel diameter of each region of interest,
the second reference information includes information indicating a relation among the generation condition of the X-ray, the corresponding concentration of the contrast agent, and the contrast for each blood vessel diameter, and
the processing circuitry is further configured to determine a blood vessel diameter in the region of interest of the subject based on the first reference information, and determine the particular concentration of the contrast agent in the blood vessel included in the contrast-enhance image to be collected based on the second reference information corresponding to the determined blood vessel diameter.

4. The X-ray diagnostic apparatus according to claim 1, wherein
the first reference information further includes information of a representative body thickness of each region of interest,
the second reference information includes information indicating a relation among the generation condition of the X-ray, the corresponding concentration of the contrast agent, and the contrast for each body thickness, and
the processing circuitry is further configured to determine a body thickness in the region of interest of the subject based on the first reference information, and determine the particular concentration of the contrast agent in the blood vessel included in the contrast-enhance image to be collected based on the second reference information corresponding to the determined body thickness.

5. The X-ray diagnostic apparatus according to claim 1, wherein
the second reference information includes information indicating a relation among the generation condition of the X-ray, the corresponding concentration of the contrast agent, and the contrast for each blood vessel diameter, and
the processing circuitry is further configured to determine a blood vessel diameter in the region of interest of the subject from a past image of the region of interest of the subject, and determine the particular concentration of the contrast agent in the blood vessel included in the contrast-enhance image to be collected based on the second reference information corresponding to the determined blood vessel diameter.

6. The X-ray diagnostic apparatus according to claim 1, wherein
the second reference information includes information indicating a relation among the generation condition of the X-ray, the corresponding concentration of the contrast agent, and the contrast for each body thickness, and
the processing circuitry is further configured to determine a body thickness in the region of interest of the subject from a past image of the region of interest of the subject, and determine the particular concentration of the contrast agent in the blood vessel included in the contrast-enhance image to be collected based on the second reference information corresponding to the determined body thickness.

7. The X-ray diagnostic apparatus according to claim 1, wherein
the setting information calculated by the processing circuitry is at least one of an injection speed of the contrast agent to be injected to the subject and a dilution ratio of the contrast agent.

8. The X-ray diagnostic apparatus according to claim 1, wherein the processing circuitry is further configured to determine a particular region of interest of the subject based on an imaging protocol of the subject.

9. The X-ray diagnostic apparatus according to claim 1, wherein the processing circuitry is further configured to determine a particular region of interest of the subject based on a size of a field of view at imaging.

10. The X-ray diagnostic apparatus according to claim 1, wherein the processing circuitry is further configured to correct the setting information based on a contrast of a past contrast-enhanced image of a particular region of interest of the subject, and on setting information of an injector at collection of the contrast-enhanced image.

11. The X-ray diagnostic apparatus according to claim 1, wherein the processing circuitry is further configured to correct the setting information based on an artifact included in a past three-dimensional contrast-enhanced image of a particular region of interest of the subject.

12. The X-ray diagnostic apparatus according to claim 1, wherein the processing circuitry is further configured to cause a display to display the setting information.

13. The X-ray diagnostic apparatus according to claim 1, wherein the processing circuitry is further configured to transmit the calculated setting information to the injector.

14. The X-ray diagnostic apparatus according to claim 13, wherein the processing circuitry is further configured to transmit the setting information, which further includes at least one of a total amount of the contrast agent, an injection time, and an injection start timing, to the injector.

15. A medical-information processing apparatus, comprising:
processing circuitry configured to
determine, before performing contrast-enhanced imaging, a particular concentration of a contrast agent in a blood vessel included in a contrast-enhanced image to be collected, based on first reference information in which a recommended contrast in a contrast-enhanced image is associated with each region of interest to be subject to collection of a contrast-enhanced image, and on second reference information that indicates a relation among a generation condition of an X-ray, a concentration of the contrast agent, and a contrast, and
calculate setting information of an injector to inject the contrast agent to the subject based on the determined concentration of the contrast agent.

* * * * *